(12) United States Patent
Pratt et al.

(10) Patent No.: US 7,923,032 B2
(45) Date of Patent: Apr. 12, 2011

(54) BUOYANT POLYMER PARTICLES FOR DELIVERY OF THERAPEUTIC AGENTS TO THE CENTRAL NERVOUS SYSTEM

(75) Inventors: Daniel Pratt, Amesbury, MA (US); Samuel S. MacAusland, Wellesley, MA (US); Keith Baker, Danvers, MA (US)

(73) Assignee: Seacoast Neuroscience, Inc., Amesbury, MA (US)

( * ) Notice: Subject to any disclaimer, the term of this patent is extended or adjusted under 35 U.S.C. 154(b) by 140 days.

(21) Appl. No.: 10/723,626

(22) Filed: Nov. 26, 2003

(65) Prior Publication Data
US 2004/0105888 A1 Jun. 3, 2004

Related U.S. Application Data

(60) Provisional application No. 60/429,854, filed on Nov. 26, 2002.

(51) Int. Cl.
| | |
|---|---|
| A61K 9/14 | (2006.01) |
| A61K 9/00 | (2006.01) |
| A61K 9/10 | (2006.01) |
| A61K 31/13 | (2006.01) |
| A61K 31/131 | (2006.01) |
| A61K 31/14 | (2006.01) |
| A61K 31/56 | (2006.01) |
| A61K 31/59 | (2006.01) |

(52) U.S. Cl. ........ 424/489; 514/167; 514/169; 514/579; 514/659; 514/728; 514/774; 514/776; 514/781; 514/947; 514/951

(58) Field of Classification Search .................. 424/489; 514/781, 776, 774, 947, 951, 167, 169, 728, 514/2
See application file for complete search history.

(56) References Cited

U.S. PATENT DOCUMENTS

| | | | | |
|---|---|---|---|---|
| 5,354,934 | A | * | 10/1994 | Pitt et al. ............................ 514/8 |
| 5,455,044 | A | | 10/1995 | Kim et al. .................... 424/450 |
| 5,560,933 | A | * | 10/1996 | Soon-Shiong et al. ........ 424/489 |
| 5,576,018 | A | | 11/1996 | Kim et al. ..................... 424/450 |
| 5,814,607 | A | * | 9/1998 | Patton ............................ 514/12 |
| 5,814,666 | A | * | 9/1998 | Green et al. .................. 514/611 |
| 6,123,956 | A | | 9/2000 | Baker |
| 6,306,439 | B1 | * | 10/2001 | Penners et al. ................ 424/469 |
| 2003/0059476 | A1 | * | 3/2003 | Wang ............................ 424/523 |
| 2003/0129233 | A1 | * | 7/2003 | Vook et al. .................... 424/470 |

(Continued)

FOREIGN PATENT DOCUMENTS
WO WO 94/26250 11/1994

OTHER PUBLICATIONS

Oxford Pocket American Dictionary of Current English, Oxford University Press: New York, 2002, p. 97.*

(Continued)

*Primary Examiner* — James H Alstrum Acevedo
(74) *Attorney, Agent, or Firm* — Mintz, Levin, Cohn, Ferris, Glovsky and Popeo, P.C.

(57) ABSTRACT

The invention provides compositions and methods for treating a subject who has suffered from a central nervous system disorder. More particularly, the invention provides sustained polymeric drug delivery systems having a polymer particle, a therapeutic agent, and a buoyancy agent for direct delivery of therapeutic agents into the central nervous system.

14 Claims, 10 Drawing Sheets

U.S. PATENT DOCUMENTS

2003/0138486 A1* 7/2003 Ouadji ............................ 424/466

OTHER PUBLICATIONS

CRC Handbook of Chemistry and Physics, 84th ed. 2003-2004, pp. 3-306 and 3-307.*
Brown, T. L. Chemistry: The Central Science, 6th ed. Prentice Hall: Englewood Cliffs, NJ, 1994, p. 18.*
Russell et al. "Allogenic Blood Stem Cells and Bone Marrow Transplantation for Acute Myelogenous Leukemia and Myelodysplasia: Influence of Stem Cell Source on Outcome," Bone Marrow Transplantation, 1999, 24, 1177-1183.*
CRC Handbook of Chemistry and Physics, 75th edition, CRC Press: Boca Raton, 1994-1995, pp. 4-50.*
Harris, D.C. Quantitative Chemical Analysis, 4th ed., W. H. Freeman and Co.: 1995, pp. 26.*
Merriam-Webster's Collegiate Dictionary, 10$^{th}$ edition, Merriam-Webster, Inc.: Springfield, Massachusetts, 1996, pp. 152.*
"Density of Cooking Oil" accessed on Aug. 19, 2010 at hypertextbook.com/facts/2000/IngaDorfman.shtml.*
Misra et al. "Incorporation of vitamin E in poly(3hydroyxbutyrate)/Bioglass composite films: effect on surface properties and cell attachment," J.R. Soc. Interface, 2009, vol. 6, pp. 401-409.*
Estebe et al., "Prolongation of Spinal Anesthesia with Bupivacaine-Loaded (DL-Lactide) Microsheres," *Anesth Analg*, (1995), 81:99-103.
Jeong et al., "Thermosensitive sol-gel reversible hydrogels," *Advance Drug Delivery Reviews*, (2002), 54:37-51.
Lee et al., "Development of oral drug delivery system using floating microspheres", *Journal of Microencapsulation*, (1999), 16(6):715-7299.
Lee et al., "Effect of adding non-volatile oil as a core material for the floating microspheres prepared by emulsion solvent diffusion method," *Journal of Microencapsulation*, (2001), 18(1):65-75.
Zentner et al., "Biodegradable block copolymers for delivery of proteins and water-insoluble drugs," *Journal of Controlled Release*, (2001), 72:203-215.
EP Search Report, Jun. 12, 2009, EP.
Adibhatla, et al., *J. Neurochem.*, 80(1):12-23 (2002).
Agut, et al., *Arzneitm, Forsch. Drug Res.*, 33(II):1045-1047 (1983).
Bawa, et al., *J. Controlled Release*, 1:259-267 (1985).
Benowitz, et al., *J. Biol. Chem.*, 273(45):29626-29634 (1998).
Brem, et al., *J. Neurosurg.*, 74:441-446 (1991).
Brown, et al., *J. Pharm. Sci.*, 72(10):1181-1185, Oct. 1983.
Camarata, et al., *Neurosurg.*, 30(3):313-319 (1992).
Chen, et al., *Proc. Natl. Acad. Sci. USA*, 99(13):9031-9036 (2002).
Fresta, et al., *Pharm. Res.*, 12(11):1769-1774 (1995).
Goodell, et al., *Am. J. Hospital Pharm.*, 43(6):1454-1461 (1986).
Göppferich, A., *Marcomolecules*, 30(9):2598-2604 (1997).
Grill, et al., *J. Neurosci.*, 17(14):5560-5572 (1997).
Hansch, et al., *J. Med. Chem.*, 11(1):1-11 (1967).
Harbaugh, R.E., *Psychopharmacol. Bulletin*, 22(1):106-109 (1986).
Hatcher, et al., *Soc. Neurosci.*, Abstract only, 25:583 (1999).
Hentze, et al., *Rev. Mol. Biotech.*, 90(1):27-53 (2002).
Kammersgaard, et al., *Stroke*, 31:2251-2256 (2000).
Kawashima, et al., *J. Controlled Release*, 16(3):279-289 (1991).
Langer, et al., *J. Macromol. Sci.—Rev. Macromol. Chem. Phys.*, C23(1):61-126 (1983).
Langer, et al., in Biomedical Polymers, polymeric materials and pharmaceuticals for biomedical useGoldberg, E.P., Nakagim, A. (eds.), Academic press, pp. 113-137 (1980).
Langer, R., *J. Controlled Release*, 16(1-2):53-59 (1991).
Lazorthes, et al., in Advances in Drug Delivery Systems and Applications in Neurosurgery, 18:143-192 (1991).
Lee, et al., *J. Microencapsualtion*, 18(1):65-75 (2001).
Lee, et al., *J. Microencapsualtion*, 16(6):715-729 (1999).
Lexin, et al., *Anesthesia and Analgesia*, 60(11):814-817 (1981).
Menei, et al., *Neurosurg.*, 34(6):1058-1064 (1994).
Noor, et al., *Med. Sci. Monit.*, 8(9):RA210-RA215 (2002).
Ommaya, A.K., *Cancer Drug Delivery*, 1(2):169-179 (1984).
Petrausch, et al., *J. Neurosci.*, 20(21):8031-8041 (2000).
Rao, et al., *J. Neurosci. Res.*, 58(5):697-705 (1999).
Rhine, et al., *J. Pharm. Sci.*, 69(3):265-270 (1980).
Secades, et al., *Meth. Find. Exp. Clin. Pharmacol.*, 17Suppl. B):1-54 (1995).
Weiss, G.B., *Life Sci.*, 56(9):637-660 (1995).
Winn, et al., *Experimental Neurol.*, 105(3):244-250 (1989).

* cited by examiner

BUOYANT POLYMER PARTICLES FOR DELIVERY OF THERAPEUTIC AGENTS TO THE CENTRAL NERVOUS SYSTEM

PRIORITY INFORMATION

This application claims priority to provisional patent application U.S. Ser. No. 60/429,854, filed on Nov. 26, 2002, the entire contents of which is hereby incorporated by reference.

BACKGROUND OF THE INVENTION

The invention provides compositions and methods for treating a subject who has suffered from a central nervous system disorder.

Historically, therapeutic intervention in neurological disorders has been limited by (1) a lack of understanding of the complicated physiological events of the disorder; (2) a lack of reliable animal models which mimic the human disorder to test product candidates; and (3) lack of adequate concentrations of drug reaching the injured brain tissue. It has been difficult to achieve effective therapeutic drug treatment of neurological disorders, because there are numerous chemical and physical barriers which must be overcome in order for such a delivery to be successful.

SUMMARY OF THE INVENTION

The invention provides polymer compositions useful for delivering therapeutic agents for preventing or providing treatment for neurological disorders.

The invention features a biodegradable polymer composition containing a therapeutic agent, a polymer and a buoyancy agent. The composition is controllably buoyant in cerebrospinal fluid (CSF).

Buoyancy is conferred by the addition of at least one buoyancy agent. The degree of buoyancy is controlled by the amount of the agent.

In one embodiment, the polymer composition is neutrally buoyant in CSF. In another embodiment, the polymer composition is positively buoyant in CSF. In yet another embodiment, the polymer composition is negatively buoyant in CSF. For example, the buoyancy agent is a gas. For example, the gas is air, i.e., the gas contains a mixture of oxygen and nitrogen. Alternatively, the buoyancy agent is a gas selected from the group consisting of nitrogen, argon, carbon dioxide, helium, and xenon. Alternatively, the buoyancy agent is a hydrofluorocarbon. An increase in positive buoyancy is achieved by increasing the amount or composition of the gas or incorporating a lighter gas.

For the treatment of ischemic events such as stroke, the invention provides a composition containing a therapeutic agent that mitigates brain damage and/or that repairs brain damage as a result of the injury. The composition contains a biodegradable polymer composition, with a therapeutic agent selected from the group consisting of inosine, citicholine, SOD and dextrorphan. For example, the composition includes a first polymeric particle comprising a first therapeutic agent and a second polymeric particle comprising a second therapeutic agent, wherein said first and said second polymeric particles comprise a buoyancy agent. The ratio of the first polymeric particle and the second polymeric particle is 50:50. Alternatively, the ratio of the first polymeric particle and the second polymeric particle is 60:40 or 40:60. Mixtures of inosine-containing and citicholine-containing particle vary, e.g., 70:30, 80:20, 90:10, 30:70, 20:80, or 10:90.

The mixtures are administered to subjects who have suffered a stroke. The amount or ratio of therapeutic agent(s) in the mixture varies depending on the length of time elapsed between the stroke event and drug administration. For example, the longer the time elapsed from ischemic event, the greater the amount of inosine (relative to citicholine) is administered. If the combination drug treatment is commenced relatively soon after an ischemic event, a greater amount of citicholine is administered in the mixture. The drug mixture is administered from one minute to one hour, to one day and up to one month following a stroke. The mixtures are delivered before, during, and after development of an ischemic cascade following a traumatic event such as stroke.

Also included in the invention is a sustained biodegradable polymer composition that is administered intrathecally to treat a subject who has been diagnosed as having a central nervous system disorder. The composition includes a plurality of polymer particles, each particle including a buoyancy agent and a therapeutic agent. The buoyancy agent allows the polymer composition to be targeted to or away from the brain or spinal cord of the subject, therefore delivering the therapeutic agent for an extended period of time to a targeted tissue to treat a subject having a central nervous system disorder.

The biodegradable polymer composition is suitable for intrathecal administration to treat a subject having a central nervous system disorder and includes a plurality of polymeric particles containing a therapeutic agent and a buoyancy agent. The polymer composition circumvents the blood-brain barrier (BBB) and circulates within the central nervous system of the subject delivering the therapeutic agent to an injured region of the brain for an extended period of time. These implantable devices are used to achieve continuous delivery of therapeutic agents directly into the brain, spinal column, or related tissues for an extended time period. The polymer compositions are applicable in the treatment of a variety of CNS disorders including, but not limited to, cancer, Parkinson's disease, Alzheimer's dementia, Huntington's disease, epilepsy, Amyotrophic Lateral Sclerosis (ALS), Multiple Scleross (MS), antibiotic delivery, trauma, stroke, Traumatic Brain Injury (TBI), cerebral ischemia, depression, spinal cord injury, pain management and other types of neurological and psychiatric illnesses.

Polymers of the invention are naturally derived polymers, such as albumin, alginate, cellulose derivatives, collagen, fibrin, gelatin, and polysaccharides as well as synthetic polymers such as polyesters (PLA, PLGA), polyethylene glycol, poloxomers, polyanhydrides, polyorthoesters, and pluronics. The polymeric carriers of the present invention are used as drug delivery vehicles. A wide variety of therapeutic agents are included in the compositions of the present invention and are described herein.

For treating central nervous system lymphomas, cancer therapeutics such as members from the following classes are delivered, either alone or in conjunction with the above-mentioned therapeutic agents: vinca alkaloids and other plant products, cytostatic drugs, cytotoxic drugs, hormones (estrogens and anti-estrogens), alkylating agents, immunomodulators (immunostimulators and immunosuppressives), hematological agents, non-steroidal products, radiopharmaceuticals, antibodies, antiandrogens, and epidermals.

The invention provides a method for distributing one or more therapeutic agents within the central nervous system of a subject. The method includes delivering within the central nervous system a polymer composition containing a plurality of polymeric particles, each particle containing one or more therapeutic agents and one or more buoyancy agents. The particles move up (positively buoyant), sink (negative buoyant) or remain generally in the region of implantation depending on the amount and/or nature of the buoyancy agents. The composition biodegrades and slowly releases the one or more therapeutic agents to the subject having a central nervous system disorder.

Specific technical and scientific terms used herein have the following meanings:

As used herein and in the claims, the singular forms "a", "and" and "the" include plural referents unless the context clearly dictates otherwise. For example, the term "a therapeutic agent" includes at least one therapeutic agent.

As used herein, "central nervous system disorder" refers to any disease state which is present in the brain, spinal column, and related tissues, such as the meninges.

As used herein, "cerebrospinal fluid", "CSF" refers to a continuous fluid system that fills the cerebral ventricles and subarachnoid space (areas that surround the brain and spinal cord). Far more than a shock absorber cushion of protection for the brain and spinal cord, the motion and flow of CSF is essential to the proper functioning of the central nervous system. CSF bathes the neurons and glial cells of the brain and spinal cord; and as such it carries nutrients as well as removes metabolic wastes and toxic substances from the central nervous system.

As used herein, "polymer" refers to molecules formed from the chemical union of two or more repeating units. For example, included within the term "polymer" are dimers, trimers and oligomers. For example, the polymer is synthetic, naturally occurring or semisynthetic. In preferred form, the term "polymer" refers to molecules which comprise 10 or more repeating units and are biodegradable.

As used herein, "sustained polymer delivery composition" refers to a polymer composition that provides continual delivery of a therapeutic agent in vivo over a period of time following administration. Preferably, delivery of a composition continues for at least several days, a week or several weeks. Sustained delivery of the therapeutic agent is demonstrated by, for example, the continued therapeutic effect of the agent over time (e.g., for an anti-inflammatory agent, sustained delivery of the agent is measured by continued reduction of fluid accumulation in the brain over time). Alternatively, sustained delivery of the therapeutic agent is monitored by detecting the presence of the therapeutic agent in vivo over time.

As used herein, "pharmaceutically acceptable" and "biocompatible" refer to compounds, materials, compositions, and/or dosage forms which are, within the scope of sound medical judgment, suitable for contact with the tissues of human beings and animals without causing any undesirable biological effects. Undesirable effects include excessive toxicity, irritation, allergic response, or other complications commensurate with a reasonable benefit/risk ratio, and which do not interact in a deleterious manner with any of the other components of the compositions in which it is contained. Examples include, but are not limited to, any and all solvents, dispersion media, coatings, polymers, antibacterial and antifungal agents, isotonic and absorption delaying agents, and the like that are physiologically compatible. Preferably, the composition is suitable for injection into the cerebrospinal fluid. Excipients include pharmaceutically acceptable stabilizers and disintegrants.

As used herein, "subject" refers to animals. The term encompasses mammals, preferably humans.

As used herein, "therapeutic agent", "therapeutic agents" are substances which alleviates a symptom of or prevents development of a disease or disorder. For example, the therapeutic agent(s) exert a beneficial biological effect in vitro and/or in vivo. The therapeutic agents may be neutral or positively or negatively charged.

As used herein, "neuroprotective agent" refers to drugs which alleviate a symptom of or prevent damage to the brain or spinal cord. For example, such damage is the result of from ischemia, stroke, convulsions, or trauma. Some agents are administered before the event, while others are administered some time after an injury. They act by a variety of mechanisms, but often directly or indirectly minimize the damage produced by endogenous excitatory amino acids.

As used herein, "intrathecal administration" means delivery into the cerebrospinal fluid bathing the spinal cord and brain. Such delivery is carried out using a variety of known techniques including lateral cerebroventricular injection through a burrhole or cisternal puncture (CP) or lumbar puncture (LP) or the like (described in Lazorthes et al. Advances in Drug Delivery Systems and Applications in Neurosurgery, 143-192 and Omaya et al., Cancer Drug Delivery, 1: 169-179, the contents of which are incorporated herein by reference). The term "lumbar region" means the region of the back lateral to the vertebral region and between the rib cage and the pelvis. The term "cisterna magna" means the area where the skull ends and the spinal cord begins at the back of the head. The term "cerebral ventricle" means the cavities in the brain that are continuous with the central canal of the spinal cord. For example, administration of a therapeutic agent to any of the above mentioned sites is achieved by direct injection of the encapsulated therapeutic agent. For injection, the encapsulated therapeutic agents of the invention is formulated in liquid solutions, preferably in physiologically compatible buffers such as Hank's solution or Ringer's solution. In addition, the therapeutic agent is formulated in solid form and redissolved or suspended immediately prior to use. Lyophilized forms are also included. In a preferred embodiment, the injection is a single "one shot" LP administration.

The present polymers are in the form of a particle. The term "particle", as used herein, refers to a three dimensional structure. Particles comprise, for example, a single molecule of a polymer, such as PLGA associated with one or more molecules of a therapeutic agent, or a complex comprising a plurality of polymer molecules in association with a therapeutic agent. A wide variety of forms may be produced by the particles of the present invention, including, but not limited to, rod-shaped devices, pellets, buttons, beads, slabs, capsules, spheres, pastes, threads of various size, films, fibers, sprays (see e.g., Goodell et al., Am. J. Hosp. Pharm. 43:1454-1461, 1986; Langer et al., "Controlled release of macromolecules from polymers", in Biomedical Polymers, Polymeric Materials and Pharmaceuticals for Biomedical Use, Goldberg, E. P., Nakagim, A. (eds.) Academic Press, pp. 113-137, 1980; Rhine et al., J. Pharm. Sci. 69:265-270, 1980; Brown et al., J. Pharm. Sci. 72:1181-1185, 1983; and Bawa et al., J. Controlled Release 1:259-267, 1985). In a preferred embodiment of the invention, therapeutic agents are provided in non-capsular formulations such as spheres, including nanospheres and microspheres (ranging from nanometers to micrometers in size).

As used herein, "lymphoma" means cancer that arises from cells of the lymphatic system. Other cancer disease states may involve a variety of cell types, including, for example, endothelial, epithelial and myocardial cells. Included among the disease states are neoplasms, cancer, leukemia and restenosis injuries.

The therapeutic agents may be embedded within the wall of the particle, encapsulated in the particle and/or attached to the particle, as desired. "Attached to" or variations thereof, as used herein in connection with the location of the therapeutic agent, means that the therapeutic agent is linked in some manner to the inside and/or the outside wall of the particle, such as through a covalent or ionic bond, or other means of chemical or electrochemical linkage or interaction. As used herein, "encapsulated in" or variations thereof as used in connection with the location of the therapeutic agent denotes that the therapeutic agent is located in the internal particle void. As used herein, "embedded within" or variations thereof as used in connection with the location of the therapeutic agent, signifies the positioning of the therapeutic agent within the particle wall.

As used herein, "comprising a therapeutic agent" denotes all of the varying types of therapeutic positioning in connection with the particle. Thus, the therapeutic agent ise positioned variably, such as, for example, entrapped within the internal void of the particle, situated between the buoyancy agent and the internal wall of the particle, incorporated onto the external surface of the particle and/or enmeshed within the particle structure itself.

The compositions of the present invention are advantageously used as delivery vehicles for therapeutic agents, particularly therapeutic agents that may have reduced or limited solubility in aqueous media. A particular advantage of the present invention is that controlled, sustained release of therapeutic agents is achieved with the compositions described herein. As discussed in greater detail below, the therapeutic agent is preferably substantially homogeneously dispersed throughout the present particles. The term "substantially homogeneously dispersed", as used herein, means that the therapeutic agent may be at least about 75% continuously dispersed throughout the particle, with about 80% continuous dispersion being preferred. More preferably, the therapeutic agent may be at least about 85% continuously dispersed throughout the particle, with about 90% continuous dispersion being even more preferred. Still more preferably, the therapeutic agent may be at least about 95% continuously dispersed throughout the particle, with about 100% continuous dispersion (i.e., complete dispersion) being especially preferred.

As used herein, "controllably buoyant" means a polymer composition that comprises at least one buoyancy agent. The composition or amount of the buoyancy agent is adjusted to target it to or away from the brain or the spinal cord (the top or the bottom of the CNS).

Other features, objects, and advantages of the invention will be apparent from the description and from the claims. Unless otherwise defined, all technical and scientific terms used herein have the same meanings as commonly understood by one of ordinary skill in the art to which the invention belongs. All patents and publications cited in this specification are incorporated by reference.

DETAILED DESCRIPTION OF THE INVENTION

Figure 1:
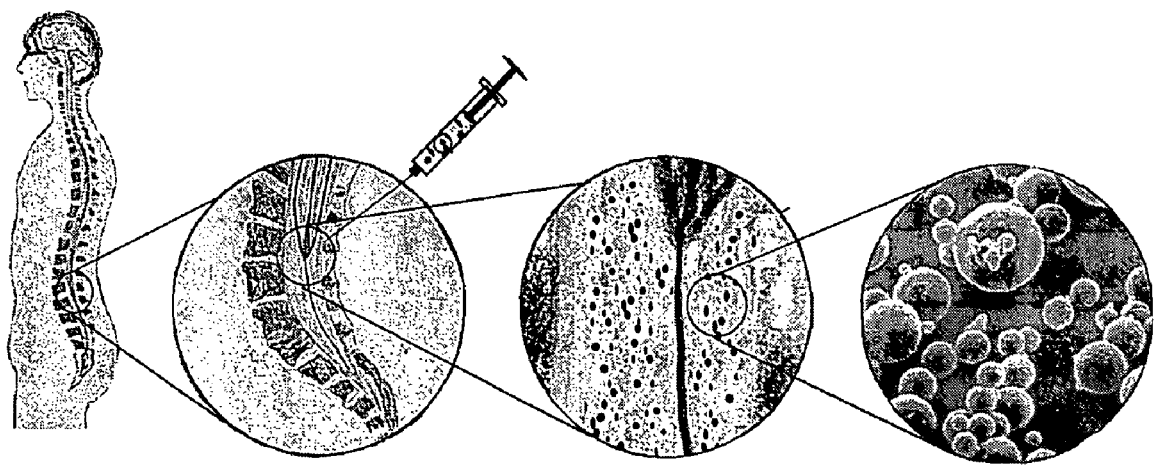
FIG. 1 is a schematic showing delivery of pharmaceutical encapsulated polymer (PEP) vehicle into the cerebrospinal fluid.

The blood brain barrier (BBB) presents the primary obstacle in delivering drugs to the brain. The BBB is composed of small blood capillaries lined with specialized endothelial cells. These small capillaries form the terminal branches of a vast network of blood vessels that deliver blood to the brain. The BBB's main purpose is to prevent pathogens from entering the CNS. The BBB prevents drugs from entering the CNS based on molecular weight, lipid solubility, and degree of ionization. Pharmaceutical companies have made numerous attempts to by-pass or force drugs through the BBB. These attempts include the disruption of the BBB by chemicals, intrathecal delivery using infusion pumps, direct delivery to the CSF through implantation of genetically engineered cells and transplantation of fetal neural tissue. Each of these methods causes undesirable side effects, as evidenced by toxic side effects, dimensional complications, lack of reliability and high cost.

Many drugs exist which pass the BBB and are therefore suitable for the treatment of certain disorders of the central nervous system (CNS). However, it has been difficult to get an adequate concentration of drug into the small blood capillaries that make up the BBB without unwanted side effects, as well as in the proper time frame necessary to effectively treat neurological diseases. In addition, there are a number of additional drugs which have potential clinical usefulness, but that do not pass through the BBB. Unfortunately, to effectively treat neurological diseases with drugs being delivered via the bloodstream, the drugs must be designed to penetrate the BBB. It is therefore desirable to develop methods to deliver drugs directly to the CNS and even to a targeted area within.

The compositions and methods of the invention provide a solution to earlier problems in delivering drugs to brain tissues because they: 1) are capable of local delivery to a targeted area such as the brain, spinal column and related tissues; 2) protect therapeutic agents from degrading to quickly; and 3) release therapeutic agents in a sustained manner.

The polymer compositions of the invention are biodegradable, non-toxic, and provide sustained delivery of therapeutic agents at an area of interest within the central nervous system (CNS). The invention differs from existing technologies in several ways: the polymer composition is fabricated from biodegradable materials and provides sustained delivery of at least one therapeutic agents over an extended time period up to several months; the site of placement of the composition is in the cerebrospinal fluid and the device is used to treat acute, traumatic neurological disorders with rapid onset of a pathologic sequence leading to cell death. Current polymeric devices for the CNS are centered on clinical targets that require implantation into a specific part of the brain parenchyma while drug is delivered over a long period of time (several months to years) to abate certain neuro-degenerative disorders (Harbaugh R. E., *Intracranial Drug Administration in Alzheimer's Disease. Psychopharmacology Bulletin* 22(1), 1986; Winn S. R. et. al., *Rats. Exp. Neuro* 105: 244-250, 1989; Langer R., *Brain. J. Cont. Rei.,* 16: 53-60, 1991; Brem H. et al. *J. Neurosurg* 74: 441-46, 1991; Camarata P. J. et al., *Neurosurgery,* 30(3): 313-19, 1992; Menei P. et al., *Neurosurgery,* 34(6):1058-64 1994).

Figure 9:
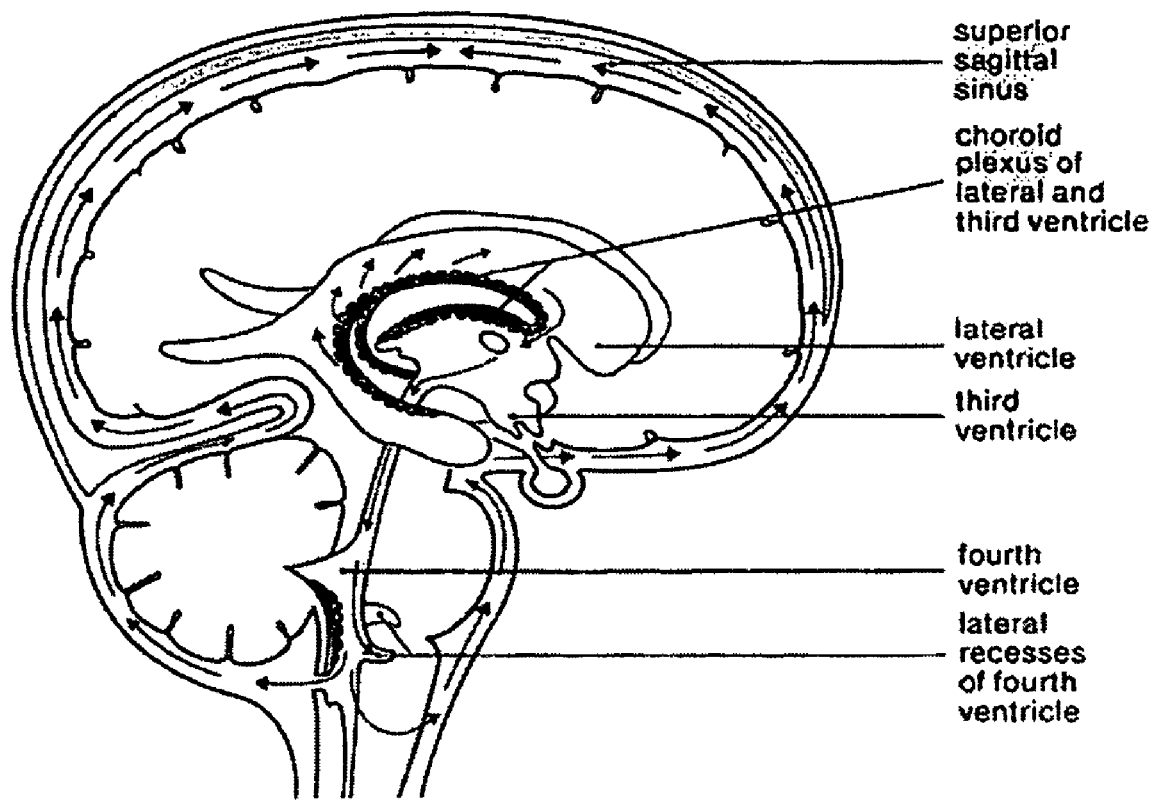
FIG. 9 is an image showing the circulation of CSF in the brain.

The compositions of the invention have all of the above-described desirable properties while, at the same time having the unique property of being controllably buoyant in cerebrospinal fluid (CSF). This unique property is accomplished by the addition of at least one buoyancy agent to the polymer composition at the time of manufacture. The buoyancy agent confers properties that allow for targeting of the compositions to or away from the brain or the spinal cord (the top or the bottom of the CNS) or within the CSF for local delivery of therapeutic agents. As the CSF circulates through the subarachnoid space and ventricles of the brain, indicated by the arrows in FIG. 9, the polymer biodegrades allowing the therapeutic agent to be released into the extracellular space of the brain on a controlled and sustained basis. The polymer also serves to protect the therapeutic agent from premature degradation.

The compositions of the invention can be made: negatively buoyant (having a specific gravity that is greater than that of CSF), neutrally buoyant (having a specific gravity that is about equal to CSF), or positively buoyant (having a specific gravity that is less than that of CSF). The specific gravity (SG) of CSF is normally about 1.0063 to about 1.0075, although those skilled in the art will recognize that the specific gravity of CSF may vary individually between subjects.

Currently, intrathecal pump delivery to administer pain medicine consists of a pump and catheter, both of which are surgically placed under the skin. A catheter connects to the pump and is tunneled under the skin to the site where medication is to be delivered. The pump releases the medication at the set rate, and the medication flows from the pump, through the catheter to the site of delivery in the intrathecal space. Intrathecal drug delivery has its drawbacks. Implanting a pump is not an inocuous procedure. It causes significant cosmetic alteration at the implant site that makes it unacceptable to many patients. The pump is a mechanical device that is prone to problems ranging from glitches and mechanical compromise, to total mechanical failure. Rare instances of catheter tip granulomas can cause significant neurological symptoms. The patient is dependent on refills of drugs and adjustment of the pump to the few professionals and delivery organizations available to do this and expertise is still developing. While implantable pumps have been proven effective, they are not likely to be widely prescribed for humans because of infection risk and tissue damage caused by accidental movement of the pump and catheter. If a patient with a pump is in an accident, the pump can stop working and the catheter can be displaced. Emergency room physicians and personnel are usually not well versed in how to deal with pump patients.

The compositions of the invention are administered by intraventricular, intrathecal or epidermal administration. The advantages of intrathecally delivering the compositions of the invention over i.v. or oral administration include: 1) the BBB is bypassed preventing systemic toxic side effects and guaranteeing that the therapeutic agent will reach the damaged brain tissue, 2) the polymer serves to protect the therapeutic agent from breaking down prematurely, 3) the therapeutic agent is released continuously from the polymer into the CSF allowing the damaged tissue to be treated over an extended time period and 4) multiple therapeutic agents can be administered and delivered simultaneously for purposes of combinational therapy. For example, antioxidants, NMDA antagonists, etc can be used.

In a preferred embodiment, the compositions are administered intrathecally via a needle either using a single "one shot" lumbar puncture (LP) or a single "one shot" cisternal puncture (CP) making it more desirable to patients as compared to intrathecal pump delivery. As the polymer composition degrades, the therapeutic agent is released slowly over time. The polymer composition also protects the therapeutic agent from premature degradation.

The compositions of the invention are easily suspended in aqueous vehicles and injected through conventional hypodermic needles. Prior to injection, the carriers can be sterilized with, preferably, gamma radiation or electron beam sterilization.

Those skilled in the art will recognize that for certain central nervous system disorders, there may be an increase in intracranial pressure (ICP), causing the force and/or weight of the circulating "CSF" to push against the meningeal membranes within which the "CSF" flows. This could have an effect on the administration of the polymer compositions of the invention, and therefore it may be necessary to: administer the polymer compositions through a shunt that is used to relieve intracranial pressure, perform a lumbar puncture (LP) to remove an equal volume of CSF to the volume of polymer composition to be administered, and to elevate the head and neck/upper torso to alleviate the extra pressure.

The appropriate dose of the therapeutic agent is that amount effective to prevent occurrence of the symptoms of the disorder or to treat some symptoms of the disorder from which the subject suffers. By "effective amount", "therapeutic amount" or "effective dose" is meant that amount sufficient to elicit the desired pharmacological or therapeutic effects, thus resulting in effective prevention or treatment of the disorder. Thus, when treating a CNS disorder, an effective amount of a therapeutic agent is an amount sufficient to pass across the BBB of the subject. Prevention of the disorder is manifested by delaying the onset of the symptoms of the disorder. Treatment of the disorder is manifested by a decrease in the symptoms associated with the disorder or an amelioration of the recurrence of the symptoms of the disorder.

The effective dose can vary, depending upon factors such as the condition of the subject, the severity of the symptoms of the disorder, and the manner in which the composition is administered. The effective dose of therapeutic agents will of course differ from subject to subject but in general includes amounts starting where CNS effects or other desired therapeutic effects occur, but below the amount where muscular effects are observed.

Typically, the effective dose of therapeutic agents generally requires administering the therapeutic agent in an amount of less than 5 mg/kg of subject weight. Often, the therapeutic agents of the present invention are administered in an amount from 1 mg to less than 100 µg/kg of subject weight, frequently between about 10 µg to less than 100 µg/kg of subject weight, and preferably between about 10 µg to about 50 µg/kg of subject weight. The foregoing effective doses typically represent that amount administered as a single dose, or as one or more doses administered over a 24-hour period.

For human subjects, the effective dose of typical therapeutic agents generally requires administering the therapeutic agent in an amount of at least about 1, often at least about 10, and frequently at least about 25 µg/24 hr./subject. For human subjects, the effective dose of typical therapeutic agents requires administering the agent which generally does not exceed about 500, often does not exceed about 400, and frequently does not exceed about 300 µg/24 hr./subject. In addition, administration of the effective dose is such that the concentration of the therapeutic agent within the plasma of the subject normally does not exceed 500 ng/ml, and frequently does not exceed 100 ng/ml.

The therapeutic agents useful according to the compositions and methods of the present invention have the ability to pass across the blood brain barrier of the subject. As such, such therapeutic agents have the ability to enter the central nervous system of the subject. The log P values of typical therapeutic agents, which are useful in carrying out the present invention are generally greater than about 0, often are greater than about 0.5, and frequently are greater than about 1. The log P values of such typical compounds generally are less than about 3.5, often are less than about 3, and sometimes are less than about 2.5. Log P values provide a measure of the ability of a therapeutic agent to pass across a diffusion barrier, such as a biological membrane. See, Hansch, et al., J. Med. Chem. 11:1 (1968).

Therapeutic agents of the present invention, when employed in effective amounts in accordance with the compositions and methods of the invention, are effective towards providing some degree of prevention of the progression of CNS disorders, amelioration of the symptoms of CNS disorders, and amelioration to some degree of the recurrence of CNS disorders. However, such effective amounts of those therapeutic agents are not sufficient to elicit any appreciable side effects, as is demonstrated by decreased effects on preparations believed to reflect effects on the cardiovascular system, or effects to skeletal muscle. As such, administration of therapeutic agents of the present invention provides a therapeutic window in which treatment of certain CNS disorders is provided, and side effects are avoided. That is, an effective dose of a therapeutic agent of the present invention is sufficient to provide the desired effects upon the CNS, but is insufficient (i.e., is not at a high enough level) to provide undesirable side effects. Preferably, effective administration of a therapeutic agent of the present invention resulting in treatment of CNS disorders occurs upon administration of less ⅓, frequently less than ⅕, and often less than 1/10, that amount sufficient to cause any side effects to a significant degree.

Polymers of the invention are naturally derived polymers, such as albumin, alginate, cellulose derivatives, collagen, fibrin, gelatin, and polysaccharides as well as synthetic polymers such as polyesters (PLA, PLGA), polyethylene glycol, poloxomers, polyanhydrides, polyorthoesters, polyanhydrides, polyurethanes, and pluronics. Polymers are designed to be flexible; the distance between the bioactive sidechains and the length of a linker between the polymer backbone and the group can be controlled.

Naturally derived polymers, such as alginate, are also used to deliver living therapeutic agents or agents that break down/become less effective as part of the manufacturing process such as bone marrow cells or fetal neural tissue or stem cells for stroke recovery because of their non-toxic make-up. Similarly, they can be used to absorb toxic substances such as calcium released in an ischemic cascade to be broken down by encapsulated calcium consuming enzymes.

The earliest of these polymers were originally intended for other, nonbiological uses, and were selected because of their desirable physical properties, for example: Poly(urethanes) for elasticity; Poly(siloxanes) or silicones for insulating ability; Poly(methyl methacrylate) for physical strength and transparency; Poly(vinyl alcohol) for hydrophilicity and strength; Poly(ethylene) for toughness and lack of swelling; and Poly(vinyl pyrrolidone) for suspension capabilities.

To be successfully used in controlled drug delivery formulations, a material must be chemically inert and free of leachable impurities. It must also have an appropriate physical structure, with minimal undesired aging, and be readily processable. Some of the materials that are currently being used or studied for controlled drug delivery include: Poly(2-hydroxy ethyl methacrylate); Poly(N-vinyl pyrrolidone); Poly (methyl methacrylate); Poly(vinyl alcohol); Poly(acrylic acid); Polyacrylamide; Poly(ethylene-co-vinyl acetate); Poly (ethylene glycol); and Poly(methacrylic acid).

However, in recent years additional polymers designed primarily for medical applications have entered the arena of controlled release. Many of these materials are designed to degrade within the body, among them: Polylactides (PLA); Polyglycolides (PGA); Poly(lactide-co-glycolides) (PLGA); Polyanhydrides; Polyorthoesters.

Factors affecting biodegradation of polymers, such as physicochemical factors (ion exchange, ionic strength, pH), will have utility. For example, when ions are released during a stroke or TBI (cerebral ischemia) certain polymers in a dose can be triggered to release their load. Some of the physicochemical factors affecting the biodegradation of the polymers include: chemical structure; chemical composition; distribution of repeat units in multimers; presence of ionic groups; presence of unexpected units or chain defects; configuration structure; molecular weight; molecular-weight distribution; morphology (amorphous/semicrystalline, microstructures, residual stresses); presence of low-molecular-weight compounds; processing conditions; annealing; sterilization process; storage history; shape; site of implantation; adsorbed and absorbed compounds (water, lipids, ions, etc.); physical factors (shape and size changes, variations of diffusion coefficients, mechanical stresses, stress- and solvent-induced cracking, etc.); and the mechanism of hydrolysis (enzymes versus water).

In a preferred embodiment, the polymer used is a poly (lactide-co-glycolide) copolymer (PLGA). The Food and Drug Administration has approved products made of PLGA (i.e. LUPRON DEPOT®, leuprolide acetate for depot suspension). Even more importantly, PLGA has shown to be non-toxic when placed in the CNS. PLGA is soluble in organic solvents. PLGA degrades by bulk hydrolysis in water as a function of the lactide:glycolide ratio and molecular weight (Langer R. et al., Chemical and physical structure of polymers as carriers for controlled release of therapeutic agents: a review, *JMS-Rev. Macromol. Chem. Phys.*, 23: 61-126, 1983; Gopferich A., Polymer bulk erosion, *Macromolecules* 30: 2598-2604, 1997.) The rate of PLGA hydrolysis controls the rate of release of an encapsulated pharmaceutical. Thus, one can control the release of a drug in a PLGA polymer matrix by varying PLGA's lactide:glycolide ratio and molecular weight. Also, by controlling various process parameters (i.e. solvent/non-solvent systems, shear rate during emulsification or hardening) it is possible to control the size of the microspheres made from the PLGA/drug matrix.

The compositions of the invention preferably contain at least 0.1% of polymer by weight. The percentage of the compositions may, of course, be varied and may conveniently be between about 2 to about 80% of the weight and preferably 2 to about 10% of a given unit dosage form. The amount of polymer in such therapeutically useful compositions is such that an effective dosage level will be obtained.

Therapeutic Agents

As discussed above, the polymer compositions of the invention are used for sustained delivery of at least one therapeutic agent. A wide variety of therapeutic agents are included in the compositions and methods of the invention, including, but not limited to ADHD drugs (methylphenidate & SR, Dexedrine & spansules, adderall, adderall XR, concerta, strattera), alkaloids, alkylating agents, alpha-2-adrenergic agonists, AMPA receptor antagonists (NBQX), amino acids, analgesics, androgens, angiogenesis inhibitors, anti-anxiety drugs, antibiotics, anticoagulants (ancrod), anti-convulsants (phenobarbital, dilantin, primidone, tegretol & XR, carbatrol, lamictal, gabitril, depakote & ER, keppra, neurontin, topamax, zarontin, trileptal), anti-depressants (amitriptyline, amoxapine, clomipramine, desipramine, doxepin, imipramine, nortriptyline, trazodone, fluxetine, lexapro, effexor, effexor XR, paxil, paxil CR, remeron sol tab, serzone, Zoloft, wellbutrin & SR), anti-emitics, anti-epileptic medications, antiestrogens, anti-inflammatory agents, anti-mania drugs, anti-metabolites, anti-panic drugs, anti-parkinson drugs (selegiline, trihexyphenidyl, bromocriptine, sinemet & CR, mirapex, requip, permax), antipsychotics (phenothiazines, thioxanthene, dibenzodiazepines, benzisoxazole, butyrophenones, indolone, diphenylbutylpiperidine), anti-psychotropic agents, antipyretics, anti-tremor drugs, antiandrogens, antibodies, antiangiogenic facots, antioxidants (superoxide dismutase (SOD), catalase, nitric oxide, mannitol), Apha-synuclein inhibitors apoptosis blockers, barbituates, bcl-2 oncogene products, beta-amyloid inhibitors, calcium channel blockers (isradipine, nicardipine, nifedipine, nimodipine, verapamil, ziconotide), calpain inhibitors, carbidopa, cardiac anti-arrhythmics, caspase inhibtors, central alpha-2 agonists, chemotherapy drugs (mechlorethamine, vincristine, procarbazine, prednisone, doxorubicin, bleomycin, vinblastine, dacarbazine), choline, cholinergic neuronotropic agents, crystalline alkaloids, local anesthetics, antihypertensive drugs, collagen synthesis inhibitor, cytokine regulator fibroblast blocker, cluster-blocking drugs, CNS mood stabilizers (lithium, eskalith CR, depakote, corticosteroids, cyclooxygenase (COX)-2 inhibitors, cytokines, cytostatic drugs, cytotoxic drugs, enzymes, epidermals, epipodophyllotoxins, estrogens, ethylene imines and methyl-melamines, excitatory amino acid antagonist or agonist, extracellular matrix proteins, folic acid analogs, free radical scavengers, gangliosides, genes, gene transcription regulators, gonadotropin-releasing hormone analogs, hematological agents, hormones, IL-1 receptor inhibitors, immunomodulators, initoxantrone, lipid peroxidation inhibitors, living cells such as bone marrow cells or fetal neural tissue or stem cells, metal co-ordination complexes and mixtures thereof, minerals, mineral supplements, monoamine agonists (amphetamines), monoamine oxidase inhibitors (MAOIs), mutant gene expression suppressors (small interfering RNA), myelin-associated neurite growth inhibitor blocker, natural anticancer products, nerve growth enhancing agents, neuroleptics, neurotransmitters (dopamine, dopamine agonists, serotonin, norepinephrine, epinephrine, histamine, acetylcholine, gamma-aminobutyric acid (GABA), glycine, glutamate, aspartate, nitric oxide (NO), carbon monoxide), neurotrophic factors (endorphins, citicholine, inosine), N-methyl-D-aspartate (NMDA) antagonists (dextrorphane, MK-801, agmatine, GK-11), neurotrophic drugs (IGF-1), neurotrophins (NGF, GDNF, CNTF, NT-3, NT-4/5, FGF, BDNF), nicotinic acetylcholine receptor (nAChR) agonists, nitrogen mustards, nitroso ureas, nitric oxide inhibitor, non-benzodiazepine anxiolytics and hypnotics, nonsteroidal anti-inflammatory drugs (NSAIDS: aspirin, acetaminophen, choline magnesium trisalicylate, diclofenac, diflunisal, fenoprofen, flurbiprofen, ibuprofen, IN-1 antibody, indomethacin, ketoprofen, meclofenamate, nabumetone, naproxen, oxaprozin, phenylbutazone, piroxicam, salsalate, sulindac, tolmetin), omega 3 oils, opioid analgesics, peptides and proteins derived from venom and associated derivatives (conopeptides, platinum complexes and mixtures thereof, potassium channel blockers (4-AP), protease inhibitors, proteosome inhibitors, purine analogs, pyrimidine analogs, radiopharmaceuticals, serotonin reuptake inhibitors (SSRIs), signal transduction modulators, skeletal muscle relaxants, sodium channel blockers, steroid anti-inflammatory drugs (cortisone, prednisone, prednisolone, dexamethasone), tetramethylpyrazine, toxic alpha-synuclein production inhibitors, tricyclic antidepressants (TCAs), trophic factors, vinca alkaloids, vitamins (such as vitamin A, vitamin B, vitamin C, vitamin D, vitamin E, and vitamin K), nerve growth factors, glycoproteins, phosphodiesterase (PDE) type 4 inhibitor, beta-agonists, cholinesterase inhibitors (Tacrine, Donepezil), monosaccharides, interferon, herbs, anti-virals, neuroactive polyunsaturated lipids (NPLs), bile molecules, GABA reuptake inhibitor, carbonic anhydrase inhibitor, Valproic acid derivatives, imidazolins, ceramide inhibitors, arginase inhibitors, cephalon derivatives, polyamine inhibitors, IFN-γ inhibitor, arginase I and II inhibitor, DNA synthesis inhibitors, statins, nicotine.

Preferred therapeutic agents for use in the compositions and methods of the invention include, inosine, citicholine, SOD, and dextrorphan.

In addition to the therapeutic agent and the pharmaceutically acceptable polymer, the compositions of the invention can comprise additional pharmaceutically acceptable carriers and/or excipients.

Central Nervous System Disorders

The compositions and methods of the invention are used to prevent and/or treat many central nervous system disorders including, but not limited to, ADD, ADHD, AIDS—Neurological Complications, Absence of the Septum Pellucidum, Acquired Epileptiform Aphasia, Acute Disseminated Encephalomyelitis, Adrenoleukodystrophy, Agenesis of the Corpus Callosum, Agnosia, Aicardi Syndrome, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Aspartame, Asperger Syndrome, Ataxia Telangiectasia, Ataxia, Attention Deficit-Hyperactivity Disorder, Autism, Autonomic Dysfunction, Back Pain, Barth Syndrome, Batten Disease, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain Aneurysm, Brain Injury, Brain and Spinal Tumors, Brown-Sequard Syndrome, Bulbospinal Muscular Atrophy, Canavan Disease, Carpal Tunnel Syndrome, Causalgia, Cavernomas, Cavernous Angioma, Cavernous Malformation, Central Cervical Cord Syndrome, Central Cord Syndrome, Central Nervous System Lymphoma, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Ischemia, Cerebral Palsy, Cerebro-Oculo-Facio-Skeletal Syndrome, Charcot-Marie-Tooth Disorder, Chiari Malformation, Chorea, Choreoacanthocytosis, Chronic Inflammatory Demyelinating Polyneuropathy (CIDP), Chronic Orthostatic Intolerance, Chronic Pain, Coffin Lowry Syndrome, Coma, including Persistent Vegetative State, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease (CIBD), Cytomegalovirus Infection, Dancing Eyes-Dancing Feet Syndrome, Dandy-Walker Syndrome, Dawson Disease, De Morsier's Syndrome, Dejerine-Klumpke Palsy, Dementia—Multi-Infarct, Dementia—Subcortical, Dementia With Lewy Bodies, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dystonias, Early Infantile Epileptic Encephalopathy, Empty Sella Syndrome, Encephalitis Lethargica, Encephalitis and Meningitis, Encephaloceles, Encephalopathy, Encephalotrigeminal Angiomatosis, Epilepsy, Erb's Palsy, Erb-Duchenne and Dejerine-Klumpke Palsies, Fabry's Disease, Fahr's Syndrome, Fainting, Familial Dysautonomia, Familial Hemangioma, Familial Idiopathic Basal Ganglia Calcification, Familial Spastic Paralysis, Febrile Seizures, Fisher Syndrome, Floppy Infant Syndrome, Friedreich's Ataxia, Gaucher's Disease, Gerstmann's Syndrome, Gerstmann-Straussler-Scheinker Disease, Giant Cell Arteritis, Giant Cell Inclusion Disease, Globoid Cell Leukodystrophy, Glossopharyngeal Neuralgia, Guillain-Barre Syndrome, HTLV-1 Associated Myelopathy, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster Oticus, Herpes Zoster, Hirayama Syndrome, Holoprosencephaly, Huntington's Disease, Hydranencephaly, Hydrocephalus, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Phytanic Acid Storage Disease, Infantile Refsum Disease, Infantile Spasms, Inflammatory Myopathy, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin syndrome, Klippel Feil Syndrome, Klippel-Trenaunay Syndrome (KTS), Klüver-Bucy Syndrome, Korsakoff's Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Meningitis, Menkes Disease, Meralgia Paresthetica, Metachromatic Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multi-Infarct Dementia, Multifocal Motor Neuropathy, Multiple Sclerosis, Multiple System Atrophy with Postural Hypotension, Multiple System Atrophy, Muscular Dystrophy, Myasthenia—Congenital, Myasthenia Gravis, Myeloclastic Diffuse Sclerosis, Myoclonic Encephalopathy of Infants, Myoclonus, Myopathy—Congenital, Myopathy—Thyrotoxic, Myopathy, Myotonia Congenita, Myotonia, Narcolepsy, Neuroacanthocytosis, Neurodegeneration with Brain Iron Accumulation, Neurofibromatosis, Neuroleptic Malignant Syndrome, Neurological Complications Of Lyme Disease, Neurological Complications of AIDS, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy—Hereditary, Neurosarcoidosis, Neurotoxicity, Nevus Cavernosus, Niemann-Pick Disease, O'Sullivan-McLeod Syndrome, Occipital Neuralgia, Occult Spinal Dysraphism Sequence, Ohtahara Syndrome, Olivopontocerebellar Atrophy, Opsoclonus Myoclonus, Orthostatic Hypotension, Overuse Syndrome, Pain—Chronic, Paraneoplastic Syndromes, Paresthesia, Parkinson's Disease, Parmyotonia Congenita, Paroxysmal Choreoathetosis, Paroxysmal Hemicrania, Parry Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Post-Polio Syndrome, Postherpetic Neuralgia, Postinfectious Encephalomyelitis, Postural Hypotension, Postural Orthostatic Tachycardia Syndrome, Postural Tachycardia Syndrome, Primary Lateral Sclerosis, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Pseudotumor Cerebri, Ramsay Hunt Syndrome Type I, Ramsay Hunt Syndrome Type II, Rasmussen's Encephalitis, Reflex Sympathetic Dystrophy Syndrome, Refsum Disease—Infantile, Refsum Disease, Repetitive Motion Disorders, Repetitive Stress Injuries, Restless Legs Syndrome, Retrovirus-Associated Myelopathy, Rett Syndrome, Reye's Syndrome, Riley-Day Syndrome, SUNCT Headache, Sacral Nerve Root Cysts, Saint Vitus Dance, Salivary Gland Disease, Sandhoff Disease, Schilder's Disease, Schizencephaly, Seizure Disorder, Septo-Optic Dysplasia, Shaken Baby Syndrome, Shingles, Shy-Drager Syndrome, Sjogren's Syndrome, Sleep Apnea, Sleeping Sickness, Soto's Syndrome, Spasticity, Spina Bifida, Spinal Cord Infarction, Spinal Cord Injury, Spinal Cord Tumors, Spinal Muscular Atrophy, Spinocerebellar Atrophy, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen Disease, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury (TBI), Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, Zellweger Syndrome. See National Institute of Neurological Disorders and Stroke website.

Central nervous system (CNS) lymphoma is defined as lymphoma limited to the cranial-spinal axis without systemic disease. Vinca alkaloids and other plant products, cytostatic drugs, cytotoxic drugs, hormones (estrogens and anti-estrogens), alkylating agents, immunomodulators (immunostimulators and immunosuppressives), hematological agents, nonsteroidal products, radiopharmaceuticals, antibodies, antiandrogens, and epidermals are just a number of therapeutic agents that can be delivered to target tissues in the CNS using the polymer compositions described herein.

Additionally, neurotrophic substances play a number of potential therapeutic roles in other neurological disorders. One of the mechanisms by which the brain repairs itself following brain damage is through the regeneration and sprouting of new neuronal connections. It has recently been shown that injections of growth promoting, neurotrophic substances, or more specifically purine nucleosides such as inosine or guanosine, enhance the rate and extent of regeneration in the brain, also known as axonal outgrowth, and bring about an enhanced degree of behavioral recovery in brain damaged animals and likely, mammals including humans.

TBI and Stroke

Traumatic Brain Injury (TBI), and Stroke are CNS disorders that are characterized by the need for immediate short-term drug therapy. Traumatic Brain Injury (TBI) is caused primarily by a traumatic blow to the head causing damage to the brain, often without penetrating the skull. The initial trauma can result in expanding hematoma, subarachnoid hemorrhage (increase in blood volume), cerebral edema (increase in interstitial fluid volume), raised intracranial pressure (ICP), and cerebral hypoxia, which can, in turn, lead to severe secondary events due to low cerebral blood flow (CBF). Half of the people with TBI die before reaching the hospital and from those that survive, a large percentage suffer serious neurological disorders. There is not much that modern medicine can do to prevent or minimize the initial damage caused by TBI. Instead, doctors invest time trying to prevent secondary brain injury and, after the patient's health stabilizes, rehabilitate the injuries.

Stroke is the destruction of brain tissue due to impaired blood supply (cerebral ischemia) caused by intracerebral hemorrhage (increase in blood volume), thrombosis (clotting), or embolism (obstruction caused by clotted blood or other foreign matter circulating in the bloodstream). Stroke is the third commonest cause of death in the United States. The deleterious effects of a stroke are comparable to those caused by TBI.

Many therapeutic agents exist today for the treatment of central nervous system (CNS) disorders including Traumatic Brain Injury (TBI), and Stroke. These include: (a) nonsteroidal anti-inflammatory agents (aspirin, acetaminophen, indomethacin, ibuprofen), (b) steroid anti-inflammatory agents (cortisone, prednisone, prednisolone, dexamethasone), (c) antioxidants (superoxide dismutase, catalase, nitric oxide, mannitol), (d) calcium channel blockers (nimodipine, nifedipine, verapamil, nicardipine, isradipine), and (e) neurotrophic factors (endorphins, citicholine).

This invention provides compositions and methods which are applied to the large clinical population suffering from CNS disorders. The pathologic sequence of events that lead to debilitating aspects of TBI and stroke are effectively treated via this protocol. Preferably, the encapsulated therapeutic agents described herein are administered to the subject in the period from the time of injury to 100 hours, preferably within 1, 2, 10, 20, or 24 hours, and more preferably within 6 to 12 hours after the traumatic brain injury (TBI) or stroke has occurred.

Figure 8:
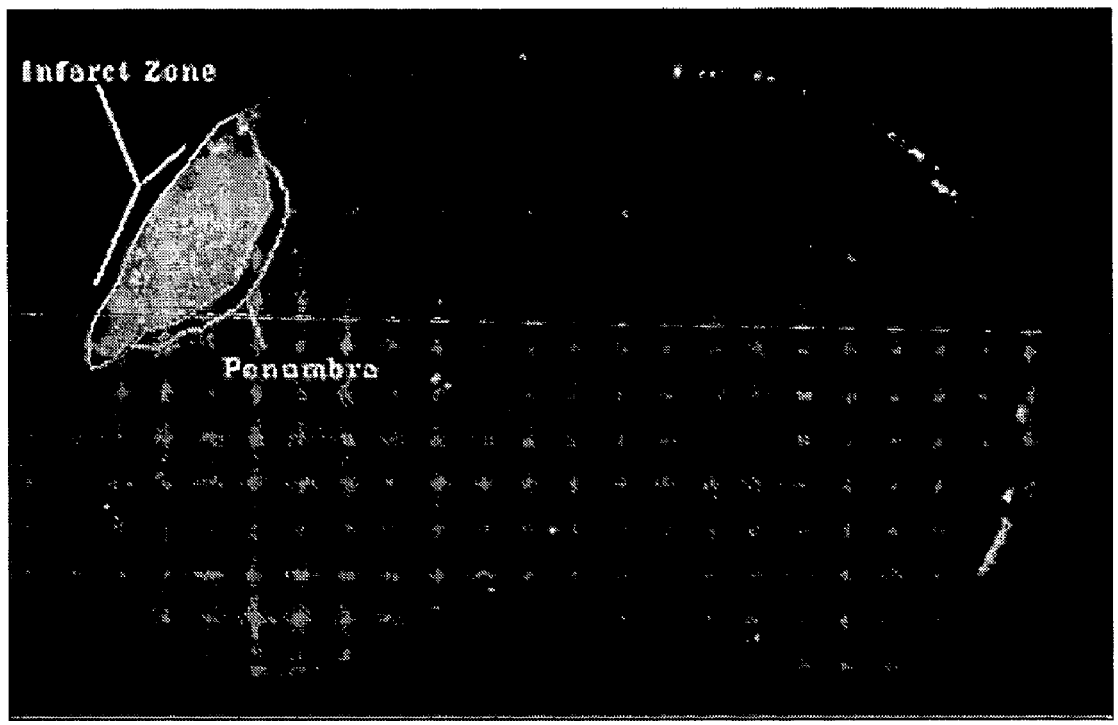
FIG. 8 is an image of cerebral ischemia in a rat brain.

Cerebral ischemia resulting from stroke or TBI is generally understood as a sequence of events (ischemic cascade) arising from a blood clot or trauma that depletes the brain of blood, oxygen, and glucose by cutting off the blood supply to a core region of brain. Cells in the core region (infarct zone) die regardless of interventional therapy (See FIG. 8). Cells on the periphery of the core region (the penumbra) are targeted for drug therapies because they are not injured as a result of the original trauma, however are at high risk from the ischemic cascade following the initial event. The therapeutic goal in acute stroke intervention has been aimed at salvaging the cells in the penumbra region, thus limiting the overall brain damage. Cells in the affected area cannot function and begin to die within minutes. The results range from mild neurological impairment, to paralysis, and even death.

Recent studies suggest that lowering the body temperature slightly within a few hours of having a stroke can reduce brain damage and risk of death. In these studies, fully conscious patients in whom modest hypothermia was achieved via surface cooling had a six-month survival rate nearly twice that of untreated control patients. See Kammersgaard et al., Stroke, 31(9):2251 (2000). Therefore, it may be desirable to administer the compositions of the invention with hypothermia, for treatment of stroke. For example, hypothermia can be induced before, after, or in conjunction with administration of the compositions of the invention. The compositions may contain more than one therapeutic agent that can be encapsulated in separate polymer compositions, or in the same polymer composition as described herein.

In certain conditions, such as hydrocephalus and edema, it may be necessary to insert a shunt to control pressure. The compositions of the invention can be administered before, after, or during shunt procedure. Those skilled in the art will recognize that the compositions of the invention can be administered before, after, or during other surgical interventions.

Combination therapy or delivery of "drug cocktails" leads to improved treatment for certain traumatic CNS injuries. In a preferred embodiment, the methods of the invention are used to treat a subject suffering from stroke. In another preferred embodiment, the method of the invention is used to treat a subject suffering from Traumatic Brain Injury (TBI). Depending upon the disease to be treated, it may be advantageous to provide more than one composition of the invention to the central nervous system. For example, a single composition may contain more than one therapeutic agent or a plurality of compositions containing different therapeutic agents may be co-administered. Also, a subject suffering from more then one central nervous system disorder is treated by the compositions of the invention.

The combination drug therapy is carried out early (from minutes (1, 2, 5, 10, 30, 45, or 60 minutes) to 3-4 hours after stroke or TBI) to late (days (1, 2, 5, or 7 days) or weeks (1, 2, 5, 7, 14, 40, or 24 weeks) after stroke or TBI) relative to the duration of the ischemic cascade.

Inosine

Inosine, a purine nucleoside, is a naturally occurring by-product of Adenosine. Inosine enters cells via facilitated diffusion or can be synthesized readily from Adenosine. In at least some neurons, inosine activates an intracellular signaling pathway that regulates the expression of multiple genes involved in axon outgrowth. Benowitz et al., J. Biol. Chem. 273: 29626-29634 (1998) and Petraush et al., J. Neurosci. 20: 8031-8041, J. Neurosci. 17: 5560-5572 (2000). In vitro and in vivo, inosine has previously been shown to induce neurons to express a set of growth-associated proteins and to extend axons with the result of axonal reorganization or "rewiring" of the brain. In adult rats with unilateral cortical infarcts, inosine stimulated neurons on the undamaged side of the brain to extend new projections to denervated areas of the midbrain and spinal cord. This growth was paralleled by improved performance on several behavioral measures. Chen et al., PNAS, 99(13): 9031-9036 (2000). Inosine promotes axonal outgrowth of damaged neurons regenerating nerve connections.

Current therapies, both approved or in development, work by minimizing the damage to the affected territory of the brain, either by reversing the blockage (by clot dissolution) or protecting brain cells from the ischemic injury (cytoprotective agents). However, once the damage is complete, there is little to no functional recovery, since there is little to no nerve regeneration in the CNS that could compensate for the irreversible loss of the nerve cells and their connections. Although the current experimental results show inosine as a very promising treatment for stroke and TBI, in these studies inosine was continuously administered (via a catheter into the ventricles) for an extended time period (from 24 hours to 28 days) using an Alzet osmotic pump.

Based on experimental results in animals, inosine effectively is preferably administered directly into the CSF, which bathes the brain. In this way, the specifically injured brain tissue is exposed to therapeutic amounts of inosine while minimizing the potential for systemic toxicity to be effective. It has been shown that inosine delivered by intravenous administration shows little or no significant recovery from limb function using the same animal model.

In order for inosine to become a universally commercial viable treatment for stroke, inosine needs to be administered directly into the CSF over an extended time period. The polymer compositions described herein, permit such extended delivery without substantial adverse side effects. The polymer compositions of the invention mediates delivery of inosine to reach injured brain tissue in adequate concentrations to confer clinical benefit to subjects suffering from a stroke. As used herein, "clinical benefit" is defined by evaluating improved cognition or motor function in an individual.

Citicholine

Citicholine (CDP-Choline or Cytidine-5'-diphosphocholine) is a small, endogenous, naturally occurring substance found in most life-forms. It is an intermediate metabolite in the major pathway phosphatidylcholine. Phosphatidylcholine is a phospholipid that is a major component of cell membranes. Phosphatidylcholine is necessary for the structure and function of all cells and is crucial for sustaining life. Citicholine supplies choline to the brain to form acetylcholine.

Citicholine is a water-soluble molecule that does appear to be efficacious in treating both acute and chronic neurological disorders including, but not limited to, TBI, stroke, head trauma, Parkinsons and Alzheimers. See Secades and Frontera Meth. Find. Exp. Clin. Pharmacol. 17: 2-54 and Weiss Life Sciences, 56(9): 637-660 (1995). See Adibhalta et al., J. Neurochemistry, 80: 12-23 (2002). Both clinical and experimental evidence has demonstrated efficacy to some moderate degree in TBI when given through the blood stream. However, citicholine rapidly hydrolyzes once in the blood stream. This fact, combined with it's polar nature, making it less likely to diffuse across the BBB freely, results in less than 1 percent of any initial dose found in the brain. This makes citicholine an ideal candidate for a polymeric carrier composition.

Citicholine has improved patient outcomes treating stroke in several clinical trails, but has shown no improvement in others. The mechanisms of action are thought to be (1) preventing fatty acid accumulation; (2) promoting recovery of brain function by providing two components, cytidine and choline, required in the formation of nerve cell membrane; (3) promoting the synthesis of acetylcholine, a neurotransmitter associated with cognitive function.

Although the current experimental results show citicholine as a very promising treatment for stroke and TBI, experiments have shown that maximum neuroprotection is obtained when citicholine is continuously administered over six days. See Hatcher et al., Soc. Neurosci. Abstract, 25: 583 (1999) and Roa et al., J. Neurosci. Res., 58: 697-705 (1999). To make citicholine a universally commercial viable treatment for TBI and stroke, it appears citicholine needs to be administered directly into the CSF over an extended time period.

When administered orally about 0.5% of the citicholine dose successfully penetrate into brain tissue. See Agut et al., Arzneim.-Forsch, 33: 1045-1047 (1983). When administered i.v., about 2% of the citicholine dose is successfully taken up into brain tissue. See Fresta et al., Pharm. Res., 12: 1769-1774 (1995). Liposomes were successfully used to increase the amount of citicholine to cross the BBB thus penetrate into brain tissue. By encapsulating citicholine with liposomes, the level citicholine reaching the brain was increased to ~23%. These results suggest that directly administering PLGA/citicholine polymeric drug delivery compositions into the CSF will greatly increase the levels of citicholine available to treat damaged brain tissue, thus greatly improving clinical outcome of citicholine treatment.

Superoxide Dismutase (SOD)

Reactive oxygen species, such as superoxide radicals, are thought to underlie the pathogenesis of various diseases. Almost 3 to 10% of the oxygen utilized by tissues is converted to its reactive intermediates, which impair the functioning of cells and tissues. Superoxide dismutase (SOD) catalyzes the conversion of single electron reduced species of molecular oxygen to hydrogen peroxide and oxygen. There are several classes of SOD that differ in their metal binding ability, distribution in different cell compartments, and sensitivity to various reagents. The enzyme from bovine and human erythrocytes contains copper and zinc, the one from chicken and rat liver mitochondria contains manganese while the enzyme from E. coli contains iron. Among these, Cu—Zn superoxide dismutase (SOD1) (Orgotein) is widely distributed and comprises 90% of the total SOD. This ubiquitous enzyme, which requires Cu and Zn for its activity, has great physiological significance and therapeutic potential. SOD has been found to play a role in numerous central nervous system disorders including, but not limited to, stroke, TBI, familial amyotrophic lateral sclerosis (FALS), Parkinson's disease, Alzheimer's disease, dengue fever, cancer, multiple sclerosis, and Down's syndrome. See Noor et al., Med Sci Monit. 8(9): RA210-5 (2002).

Except for inosine, all current therapies (both approved or in development) are focused on minimizing the damage to the affected territory of the brain, either by reversing the blockage (by clot dissolution) or protecting brain cells from the ischemic injury (cytoprotective agents). However, once the damage is complete, there is little to no functional recovery, since there is little to no nerve regeneration in the CNS that could compensate for the irreversible loss of the nerve cells and their connections. Until now, the inability to provide regeneration therapy for stroke and TBI has been due to the absence of any effective compounds having the necessary in vivo regenerative activity.

In a preferred embodiment of the invention, inosine and citicholine are attached to a polymer composition (in the same or separate particles) for the treatment of a stroke. Optionally, disease or traumatic injury is treated with a mixture of particles containing at least one, preferably two, three, or more therapeutic agents to the central nervous system.

Size of Polymeric Particles of the Invention:

In a preferred embodiment, the polymeric particles of the invention are spheres, although other forms of particles are included within the scope of the invention as described above. To maximize universal delivery, manufacturing spheres to the appropriate size to release their load in a controlled manor is advantageous. To illustrate, smaller sphere's release more quickly than larger ones allowing for a sustained release profile when a dose of various sizes is delivered. Ranges of size can be controlled with a sonication time and speed as well as other mixing techniques. Sizes range infinitely and can be selected from a batch through common techniques such as filtration. Polymeric carriers which can flow freely in the CSF are about 25 μm due to anatomical size limitations. Polymeric microspheres used in this invention as the carrier have a diameter of less than 100 μm, preferably having a size ranging from about 0.1 to about 100 μm in diameter. Even though the microsphere can be of any size, the preferred size is 1-100 μm, more preferably 2-75 μm, more preferably 3-50 μm, and even more preferably about 5-25 μm.

Preferred sizes for nanospheres range from about 1 nanometer (nm) to about 100,000 nm in diameter. Optimally preferred diameters are within about 10 and 1,000 nm, preferably within 100 and 800 nm, and more preferably within 200 and 500 nm.

Buoyancy of Particles:

The proper buoyancy—positive, neutral, or negative—of spheres ensures that the spheres minimize and control the likelihood of collision and/or aggregation. When spheres flow more freely than overly negatively buoyant spheres, collision is minimized, and collision and/or aggregation can interfere with their degradation. When spheres collide and/or aggregate, the result is a net decrease of surface area, resulting in increased variability of the release rate.

Buoyancy is adjusted to target the spheres and their agent(s) to or away from the brain or the spinal cord (the top or the bottom of the CNS). Buoyancy of the particles is engineered with negative buoyancy such that the spheres aggregate in the sacral spine following administration. Such particles are useful for delivery of pain medications for a ruptured disk for treatment of sacral spinal cord injury. Likewise, positively buoyant particles aggregate around the brain to support therapeutic agents that have specificity (particularly cancer antagonists/blockers that bind to agonists/tags/triggers) characteristics making them more efficacious or citicholine for treatment of stroke where it is advantageous to have speedy delivery. Buoyancy can range infinitely and are altered with the addition or elimination of buoyancy agents such as air, inert gas, oil, and/or other substances that are lighter than water or cerebral spinal fluid and can be adjusted by adjusting the hardening time.

With a 95% confidence limit, the specific gravity (SG) of normal human CSF at 37° C. ranges from 1.0063 to 1.0075. See Levin et al., Anesth Analg. 60(11):814-7 (1981). Those skilled in the art will recognize that the SG of human CSF will vary to a small extent individually.

To move particles towards and concentrate at the brain and upper regions of the central nervous system, particles are made positively buoyant, have a specific gravity less than 1.0063. Particles are made positively buoyant by adding one or more of the following excipients to the polymer matrix: Non-Volatile Oils: mineral oil, isopropyl myrisate, LIBRAFIL 1944™ (oleoyl macrogol-6 glycerides), vegetable oil, glyceryl monostearate, parrafin, oelic acid, methyl oelate, lanolin, petrolatin, cetyl alcohol, fish oil, corn oil, soybean oil, vitamin E, polyalkyleneglycol such as polyethyleneglycol of various molecular weights, and castor oil.

Gases: Air, Nitrogen, Argon, Hydrofluorocarbons, Carbon Dioxide, Helium, and Xenon.

To have particles remain neutrally buoyant and have the ability to be carried throughout the CNS by the natural flow of the CSF, particles must have a specific gravity between 1.0063 and 1.0075. Particles are made neutrally buoyant by adding one or more of the following excipients to the polymer matrix; Polysorbates, Sorbitan Esters, and Polyoxyethylene Alkyl Ethyls.

To move particles towards and concentrate at the spinal cord and lower regions of the central nervous system, particles are made negatively buoyant, have a specific gravity greater than 1.0075. Particles are made negatively buoyant by adding one or more of the following excipients to the polymer matrix; Glycerin, Aliphatic Polyesters, Gelatin, and Mannitol.

Methods to make microspheres positively buoyant in the gastrointestinal tract are described in Lee et al., J. Microencapsulation, 2001, 18:1, 65-75; Crotts et al., J. Controlled Release", 1995, 35, 95-105; Kawashima et al., J. Controlled Release, 1991, 16, 279-290; and Lee et al., J. Microencapsulation, 16, 715-729.

Also within the scope of the invention is the use of sonic energy, microwave energy, magnetic energy, or light energy, to help move the compositions of the invention to specific tissues.

Manufacturing of Particles:

Spheres are prepared using standard methods, e.g., those described by Sandler, S. R.; Karo, W. Polymer Syntheses; Harcourt Brace: Boston, 1994; Shalaby, W.; Ikada, Y.; Langer, R.; Williams, J. Polymers of Biological and Biomedical Significance (ACS Symposium Series 540; American Chemical Society: Washington, D.C., 1994); and H.-P. Hentze, H. P. & Antonietti, M. Porus Polymers and Resins for Biotechnological and Biomedical Applications—Review in Molecular Biotechnology, 2002. Polymers are designed to be flexible; the distance between the bioactive sidechains and the length of a linker between the polymer backbone and the group can be controlled. Other suitable polymers and methods for their preparation are described in U.S. Pat. Nos. 5,455,044 and 5,576,018. Those skilled in the art will recognize that the polymeric carriers can be formed into various shapes, as described above.

The invention will be further described in the following examples, which do not limit the scope of the invention described in the claims.

EXAMPLES

Example 1

Preparation of Polymer
Compositions—Microspheres

Various methods for preparing the polymeric particles of the present invention will be readily apparent to those skilled in the art, once armed with the present disclosure. Preferred methods for preparing the carriers are discussed below in connection with the preferred PLGA polymeric delivery systems.

Specifically, in a preferred embodiment, a method for manufacturing polymer microspheres comprising at least one therapeutic agent and at least one buoyancy agent comprises the steps of: milling and/or sieving the therapeutic agent to the desired size range (about 5 µm or less), dissolving the polymer solution in methylene chloride, or another suitable solvent, (to make a 10% polymer/solvent solution), dispersing the therapeutic agent (e.g., Inosine) in polymer solution by stirring and/or shaking, stirring the agent/polymer solution while adding silicone oil to create an emulsion, slowly (drop wise) adding the emulsion to hexane containing 0.5% w/w SPAN® 85 (sorbitan trioleate) that is being stirred rapidly and being sonicated by a sonic dismembrator, adding the appropriate amount of buoyancy agent, by mixing and/or agitating in a way to achieve desired buoyancy, briefly sonciating and stirring for 20 minutes. The spheres are then left to settle for about 5 minutes after which the excess hexane is sucked off. Then 0.5% SPAN® 85 (sorbitan trioleate)-hexane solution is added bringing the total volume to 500 ml. The microspheres are re-suspended, briefly sonicated and stirred for 20 minutes. This process of settling and adding is repeated a few times until the desired range of sizes of microspheres is achieved. The microspheres are then vacuum dried overnight.

Figure 2:
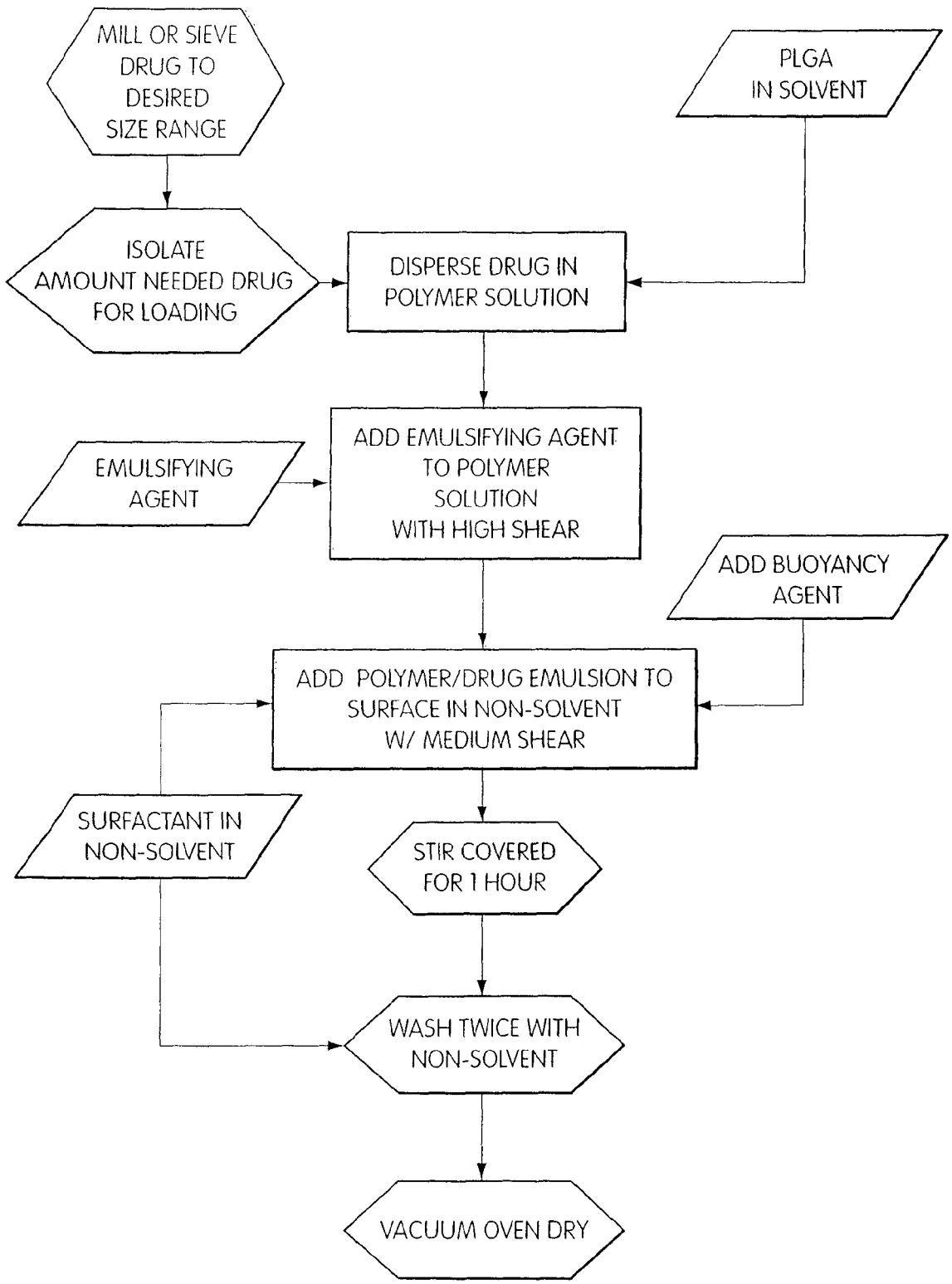
FIG. 2 is a general process flow diagram of the process of solvent evaporation to produce PLGA pharmaceutical encapsulated polymer vehicle.

FIG. 2 shows a general process flow diagram of the preliminary process. By modifying the critical process parameters of the preliminary process, microspheres of three different sizes (about 1 µm, about 10 µm, about 25 µm) were made. The size of microspheres are modified by the following parameters: shear force applied to emulsify drug/polymer/solvent in emulsifying non-solvent; ratio of drug/polymer/solvent to hardening non-solvent and substitution of solvent and non-solvent chemicals.

The release profile of drug from PLGA/drug PCs can be manipulated by the following process parameters: ratio of drug to PLGA ("Drug Loading"); molecular weight of PLGA and ratio of Lactide to Glycolide in PLGA.

Figure 10:
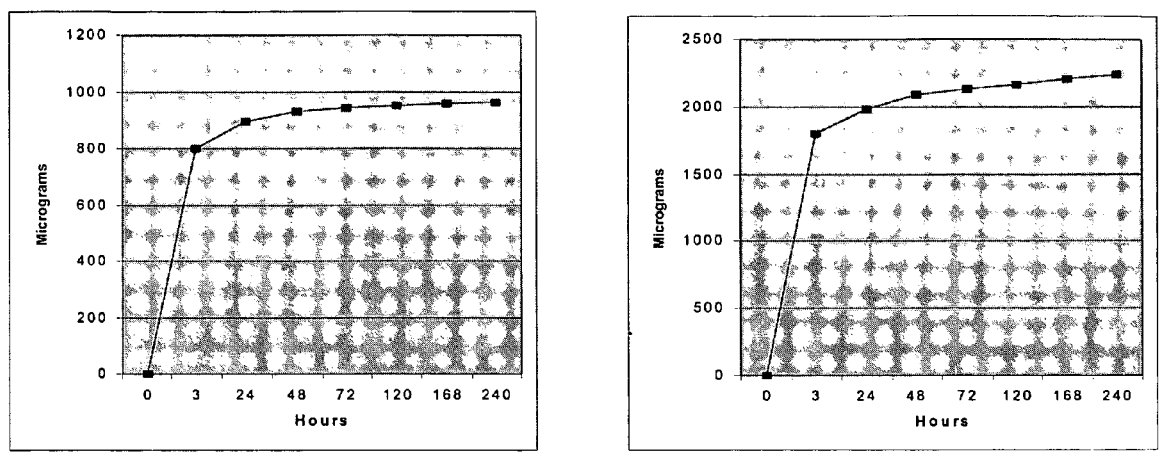
FIG. 10 is a graph showing inosine release from a composition of the invention.

The size of microspheres is determined using microscopy techniques. High performance liquid chromatography (HPLC) is used to quantify and determine release profiles. 5 ml of 10 mM PBS was added to PLGA/Inosine microspheres, that were manufactured using either ethyl acetate or methylene chloride as the solvent. After about 3 hours, 4 mL of PBS was drawn off the sample and replaced with 4 mL of fresh PBS. This procedure was repeated at the end of each time interval. Inosine concentration for the 4 mL aliquot of PBS was determined by HPLC analysis. The cumulative amounts of inosine released over 10 days and release profiles are found in FIG. 10. Results indicate that for microspheres manufactured using ethyl Acetate, 23.8% of the total inosine was released over 10 days. Microspheres manufactured using methylene chloride had about 44.2% of total inosine released over the 10 day period.

Final determination of optimal size and release profiles, along with optimal route of administration is made by testing and evaluating the distribution of drug and PC distribution in-vivo.

Figure 3:
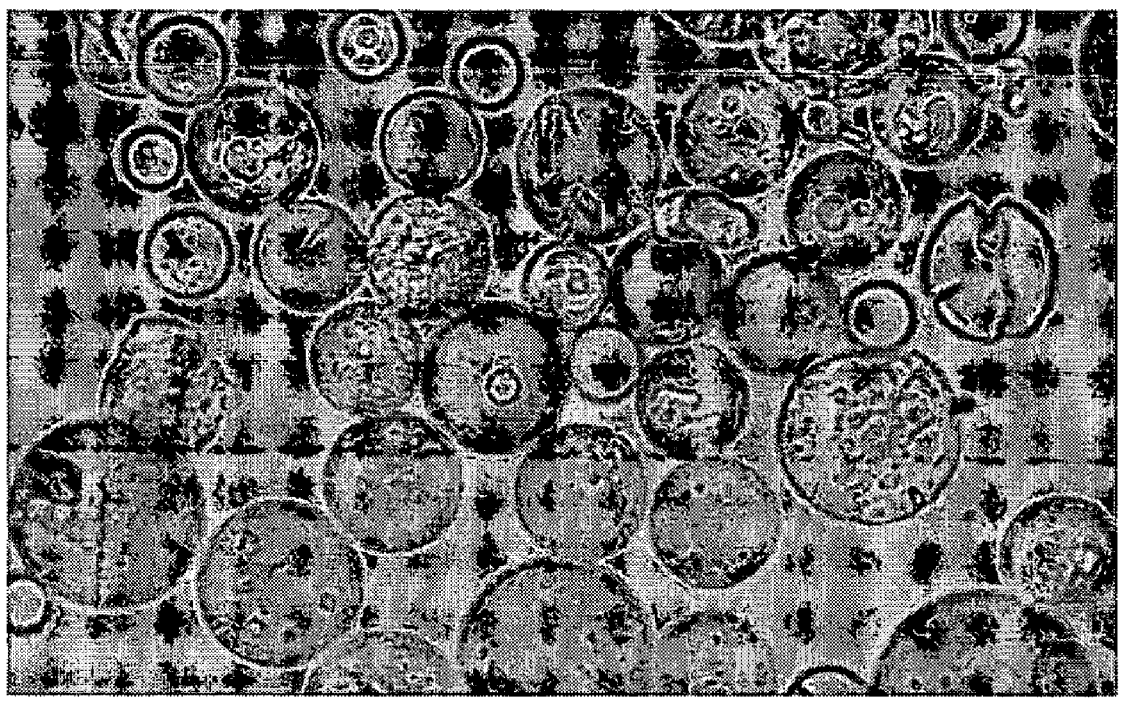
FIG. 3 is an image of PLGA/Inosine PCs.

In one example, PLGA/Inosine PCs were developed. Appropriate steps are taken to ensure full solubility of Inosine to avoid crystallization which can result in release profile variability. FIG. 3 shows an image of PLGA/Inosine PCs.

Example 2

Investigating the Anatomical Distribution of Drug and Flourescein Loaded PCs

This experiment utilizes rats, allowing for PCs to circulate in the cerebrospinal fluid (CSF). The animals are studied in 6 groups of 3. One half of the animals, 3 groups, are administered fluorescein and are sacrificed for imaging after 48 hours to study distribution of spheres in CSF, spinal cord, and brain. The other half of the animals, 3 groups, are administered with drug-loaded PCs and are sacrificed for imaging after one week to determine the concentration of drug in the CSF, spinal cord, and brain. The amount of fluorescein loaded into the PCs is determined by testing different amounts of fluorescein for microsphere fluorescence and encapsulation efficiency.

Animals are fasted from solid food for twelve hours prior to the study. Animals are pre-medicated with 6 mg/kg xylazine (2-(2,6-Dimethylphenylamino)-5,6-dihydro-4H-thiazine), sq., and are anesthetized with a mixture of xylazine, 10 mg/ml, and ketamine, 40 mg/ml, iv to effect. They are then intubated and transitioned to inhalation anesthesia, 1-2% halothane in $O_2/N_2O$, 2/1, for the duration of the study.

Various routes of administration are tested. Among these various routes are intraventricular administration. Under sterile conditions, the scalp is opened in the midline and the skin and underlying muscle reflected laterally to expose the skull. Under stereotactic guidance a neurosurgical burr is used to remove a small amount of skull bone and expose the dura. Then, under stereotactic control, a catheter is introduced into the area of interest, the lateral ventricle, both ventricles, and/or the subarachnoid space(s). Drug is then infused in various doses into the areas of interest. Animals to be recovered will have the hole in the skull packed with sterile GELFOAM® (absorbable gelatin), the muscles of the scalp closed in layers, and the skin closed with a running subcuticular suture.

In Cisterna Magna Administration (cisternal puncture), a sterile syringe with a 48 gauge needle is loaded with a PC formulation. Fur is closely shaved. Skin is cleansed and painted with iodine. The sterile needle is inserted between the cervical vertebra, through dura mater into the cisterna at the base of the brain. The designated volume of PC formulation is then infused.

In the method of Intraspinal Administration (lumbar puncture), a sterile syringe with a 48 gauge needle is loaded with a PC formulation. Fur is closely shaved. Skin is cleansed and painted with iodine. The sterile puncture needle is passed directly in the midline, to and through the dura. The designated volume of PC formulation is then infused.

Fluorescien particle Distribution is carried out as follows. After 48 hours, the animals that have been administered fluorescien particles are sacrificed under general anesthesia. The brain and spinal cord are carefully removed, fixed in 10% buffered formalin, and sectioned into slices. The slices are then placed on the microscope and imaged using fluorescence filters to indicate the distribution of spheres in CSF, spinal cord, and brain.

Drug Distribution is evaluated as follows. After seven days, the animals administered drug particles are sacrificed under general anesthesia. The CSF is then sampled, and the brain and spinal cord are carefully removed. Concentration of drug in tissue and CSF is quantified using high performance liquid chromatography. Spectra graphs of individual analytical samples is archived to record results.

Example 3

Intrathecal Administration of PLGA/Drug PCs in an Established Stroke Animal Model Intrathecal administration of PLGA/Drug particles is compared to both a bolus injection of drug and intraventricular pump delivery of drug in a rat middle cerebral artery occlusion (MCAo) stroke model. The drug is administered by three methods:
1) Pump: Drug is administered into the ventricle using an Alza osmotic pump (#2001 D) at a flow rate of 8 ul/hr over 24 hours.
2) Lumbar Puncture: A bolus of drug is injected into the CSF via the lumber region of the spine.
3) Drug/PLGA PCs: Drug/PLGA particles are administered by one of the methods described in Example 2.

Rats are used, because they are the smallest animal available with a spinal canal large enough to allow particles to circulate in the CSF. The animals will be studied in 3 groups of 12, plus control.

Rats are anesthetized with an intramuscular 4 ml/kg "cocktail" of Ketamine (25 mg/ml), Xylazine (1.3 mg/mL) and Acepromazine (0.33 mg/mL). The common carotid arteries are exposed through a ventral midline cervical incision in the neck. The temporalis muscle is bisected and reflected through an incision performed midway between the eye and the ear drum canal. A 3 mm burr hole is made at the junction of the zygomatic arch and the squamos bone such that the bifurcation of the frontal and parietal branch of the middle cerebral artery is exposed. The left middle cerebral artery is permanently occluded using a 10-0 nylon suture directly below the bifurcation of the frontal and parietal branch. Immediately after the MCAo, the common carotid arteries are temporarily occluded using atraumatic aneurysm clips for one hour. Body temperature is maintained at 38° C.±1 throughout the entire procedure. Animals are sacrificed twenty-four hours from the time of MCA occlusion and the brains are removed for histological analysis.

Morphometric analysis is performed twenty-four hours after the induction of focal ischemia. Rats are deeply anesthetized with $CO_2$ and decapitated. The brain is removed and placed in ice chilled (~4° C.) saline for fifteen minutes. Seven 2.0 mm coronal slices are cut using a brain cutting matrix and incubated in two percent 2,3,5 triphenyltetrazolium chloride (TTC) for 20 minutes at 37° C. Slices are removed, washed in saline and put into 10% formalin for 24 hours before tissue analysis.

TTC is an established marker for functional mitochondrial enzymes and produces a visible deep red color within normal tissue. Ischemic tissue, lacking mitochondrial activity, remains unstained and appears white. This is a standard method for use in image analysis of the sliced brain and quantification of the ischemic area after MCAo.

Using the IMAGE PRO-PLUS® (scientific image processing and analysis software from Media Cybernetics), a total of 14 images per brain of both the frontal and posterior side of each slice are analyzed through digital analysis. Digitizing and computation is done under blinded conditions. The total infarct volume is calculated for the left hemisphere using the equation below.

$$\text{Volume (mm}^3\text{)} = \frac{\Sigma \text{ area (mm}^2\text{) per side}}{\text{No. of sides analyzed}} \times 14 \text{ mm}$$

The total infarct volumes are calculated for each animal and subsequent group means are determined as volume of area (mm$^3$). Data is normalized to individual studies on a day to day basis because of the variation in the cerebral vasculature in different rats and operating room conditions of that day. This results in less variability within each study. Statistical analysis is performed using a two-tailed t-test and Dunnett's multiple comparison's.

Example 4

Process to Scale-Up Production of PLGA/Drug Particles for 3 Months of Stability

Production of drug-loaded polymers is carried out as follows.

The microencapsulation process used is reproducible with the capability of being scaled-up to support clinical trials. This process utilizes solvents and non-solvents that are safe.

After microencapsulation, particles of desired size are isolated from the non-solvent using techniques such as centrifugation and tangential filtration.

Formulations are stable for at least three months under standard condition. Size of microspheres are determined by microscopy. Photographs are taken to record results. High performance liquid chromatography is used to determine release profiles. Microspheres were manufactured according to Example 1 using either ethyl acetate or methylene chloride as the solvent. 5 mL of 10 mM PBS buffer was added to the microspheres. After 3 hours, 4 mL of PBS was drawn off the sample and replaced with 4 mL of fresh PBS. This procedure was repeated at the end of each time interval. Inosine concentration for the 4 mL aliquot of PBS was determined by HPLC analysis. The cumulative amounts of inosine released over 10 days was determined, see FIG. 10. Microspheres manufactured using ethyl acetate had about 23.8% of the total loaded inosine released after 10 days. Microspheres manufactured using methylene chloride had about 44.2% of the total loaded inosine released after 10 days.

Final determination of optimal size and adequate release profiles, along with optimal route of administration (as determined from Example 2), are made by testing and evaluating the distribution of Drug and PC distribution in vivo (Example 3).

Example 5

Delivery of Neuroprotectant Agents into the CSF in a Rat Middle Cerebral Artery Occlusion (MCAo) Stroke Model The parietal branch of the middle cerebral artery of the Sprague-Dawley rat is permanently occluded with a 10-0 nylon suture. The common carotid arteries are occluded temporarily for one hour. All drugs and vehicle are given beginning two hours post ischemia. Rats are sacrificed 24-hours later and the size of the infarct measured as a percent infarction of the total volume of the brain (mm$^3$) using imaging analysis. Prior to MCAo, drugs are administered into the ventricle using an Alza osmotic pump (#20010) at a flow rate of 8 ul/hr over 24 hours. A few drugs demonstrated efficacy in this model when delivered directly to the CSF (FIG. 4).

Figure 4:
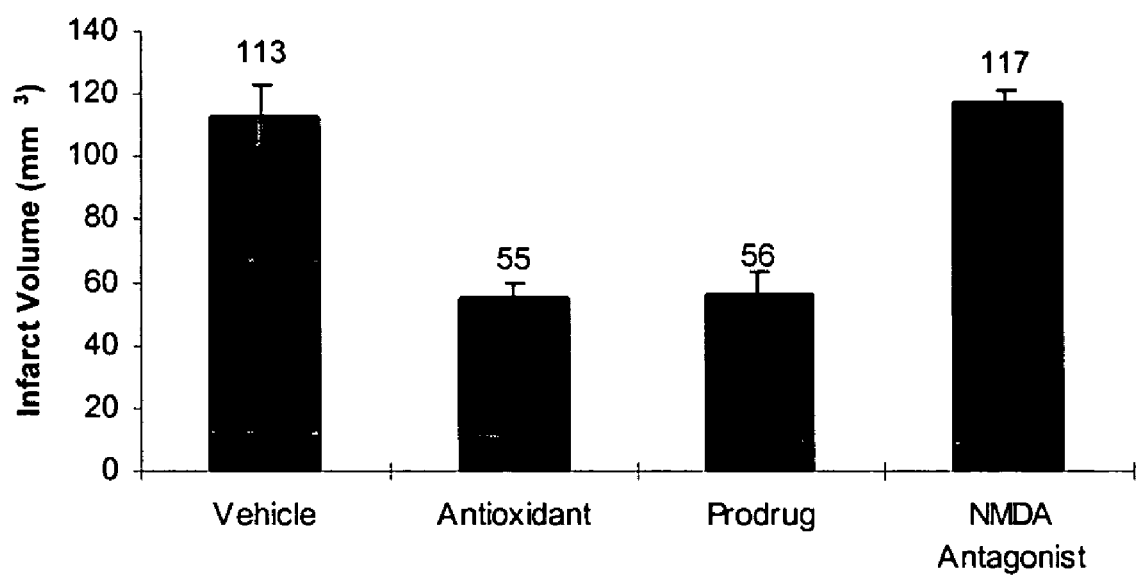
FIG. 4 is a bar graph showing efficacy results after administration of various agents in a MCAo rat model of focal cerebral ischemia by supracortical perfusion of the cortex.

FIG. 4 shows the infarct volume (mean±S.E.M.) pooled from different studies each of which included control animals. Animals were treated with vehicle (n=23), Antioxidant (n=8), Prodrug (n=7) or an NMDA antagonist (n=7). All three test agents (Antioxidant, Prodrug and NMDA antagonist) were significantly different than the vehicle treated group (P<0.01).

Figure 5:
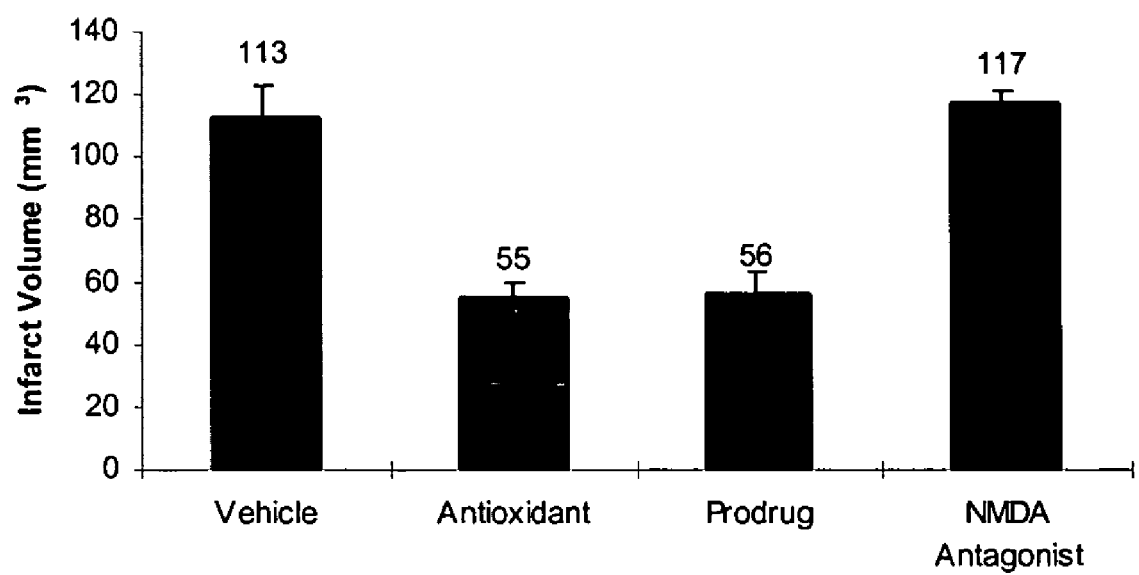
FIG. 5 is a bar graph showing the dose-response curve for citicholine administered directly into the cerebrospinal fluid of rats using the rat middle cerebral artery occlusion (MCAo) model.

Further studies with Citicholine established a dose response effect when given within the CSF (FIG. 5).

Squares of regenerated cellulose, polymer, cut into 1 mm sections are incubated at 37° C. in the different concentrations of drug solutions for approximately 24 hours before being placed on the rat cortex. A 1×1 cm section of bone over the parieto-temporal region of the rat brain is removed. The underlying dura is reflected and the pre-soaked squares are placed over the prospective infracted temporal-parietal region of the rat cortex. The overlying skin is sutured and animals are returned to their cages.

In the MCAo rat model, the largest cortical infarct is apparent at 18 hours to three days after MCAo. A small lesion appears at three hours post MCAo and progresses rapidly by six hours to a sub-maximal infarct, which is not statistically different than the 24 hour time period. Therefore the regenerated cellulose-containing drug is placed on the rat cortex two hours post MCAo. The results are summarized in FIG. 6.

Figure 6:
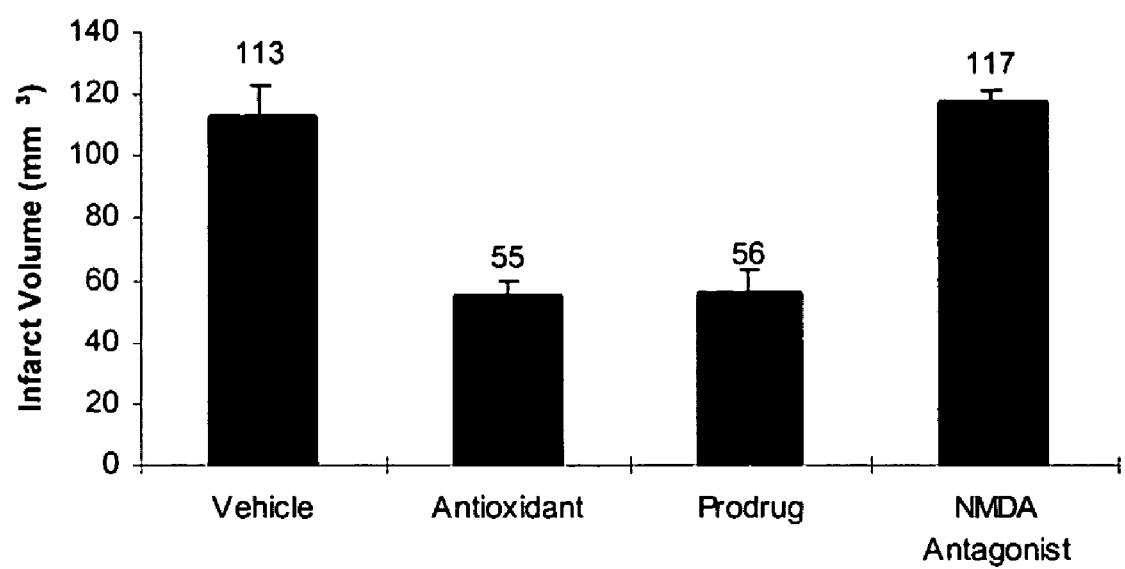
FIG. 6 is a bar graph showing the effects of the various neuroprotectant agents on infarct volume in a rat model of focal ischemia when delivered by the Supracortical perfusion method.

FIG. 6 shows the effects of the various neuroprotectant agents on infarct volume in a rat model of focal ischemia when delivered by the Supracortical perfusion method. Test compound in 0.9% saline or vehicle alone began two hours after MCAo. The figure shows infarct volume (mean±S.E.M.) pooled from different studies each of which included control animals. Animals were treated with vehicle (n=23), Super Oxide Dismutase (n=8), Citicholine (n=7) or Dextromethorphan (n=7). All three test agents were significantly different than the treated group (P<0.01).

Example 6

Inosine Stimulates Rewiring of Brain Circuits after Stroke

In one model, one side of the corticospinal tract in rats is severed as it courses through the brainstem. Inosine is then infused directly into the motor cortex of the brain, the site of origin for those axons descending into the non-injured side of the corticospinal tract. After 14 days of treatment, newly grown axon branches are traced by injecting a dye into the treated nerve cells in the cortex. Animals are then sacrificed and the spinal cord examined for histology evidence of new axon growth.

Almost all of the treated animals showed signs of extensive collateral sprouting of axons from the uninjured to the injured side of the corticospinal tract reaching below the level of the hemi-transection. These new axonal branches then continued to descend down the injured side of the corticospinal tract, effectively replacing severed axons with new ones. These axons were found to enter the gray matter of the spinal cord in a normal fashion. The number of collateral (new) axons ranged up to 2,500 per treated animal, compared to 28-170 axons seen in control animals. These data indicate that the corticospinal tract was extensively reconstituted following injury. This data was obtained using an animal model of spinal cord injury in humans.

Figure 7:
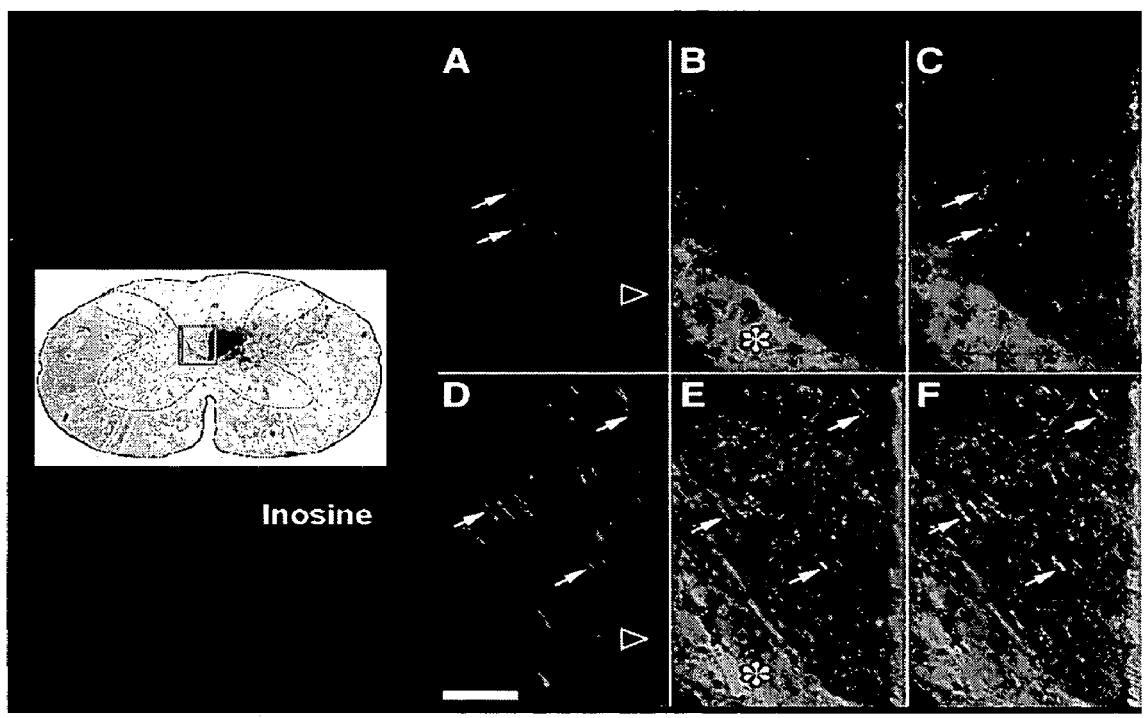
FIG. 7 is an image showing that Inosine stimulates nerve cells in undamaged parts of the brain to grow new connections into brain areas that had lost their normal connections as a result of a stroke.

FIG. 7 shows a section through the spinal cord (cervical enlargement). Area enlarged in A-F is shown by red box. A-C: Double-labeled section from a control animal treated with saline after stroke. D-F: Similarly stained sections from an animal treated with inosine after stroke. A: After stroke, animals not treated with inosine show very few axons that project from the intact hemisphere to the side of the spinal cord which lost its normal input after stroke. D: Inosine treatment causes many axons (red) to cross over from the undamaged side of the brain to the denervated side of the spinal cord (arrows). B, E: The same sections, stained with antibodies to the growth-associated protein GAP-43, show very few newly growing axons on the denervated side of the brain, but many in animals treated with inosine. C, F: Merged images showing coincidence of BDA- and GAP-43 labeled fibers (yellow staining: arrows). The midline and medial-most fibers of the intact CST are on the far right side of each frame. Scale bar 100 μm. See P. Chen et al., *PNAS*, 99(13): 9031-9036, 2002.

Example 7

A TBI Injury Model Utilizing the Dragonfly Lateral Fluid Percussion Device

The development of a TBI injury model utilizing the Dragonfly lateral fluid percussion device to create moderate to severe traumatic brain injury in rats, is necessary to standardize the procedure and establish a baseline for untreated injury to the brain parenchyma. Traumatic injury to the rat brain is performed using a modification of the lateral fluid percussion method first described by Macintosh et al. (Benowitz, L. I. et al., *J. Biol. Chem.* 273: 29626-29634, 1998; Petrausch, B. et al. *J. Neurosci.* 20: 8031-8041, 2000; *J. Neurosci.* 17: 5560-5572; P. Chen et al., Inosine induces axonal rewiring and improves behavioral outcome after stroke, *PNAS*, 99(13): 9031-9036, 2002).

Male Sprague-Dawley rats (300-350 g) are anesthetized with either an intramuscular injection of chloral hydrate 4 mg/kg or a ketamine, xylazine and acepromazine cocktail. The head is shaved then prepped and mounted in a stereotaxic frame. Body temperature is maintained at 37±0.5° C. during the procedure using a heating blanket connected to a temperature controller. A midline incision centered over the left parietal cortex is performed. When the skull dries, suture lines appear. A 2 mm diameter craniotomy is made at the level of the right parietal cortex (3.5 mm anterior to, 6 mm above the interaural line); the dura is left intact at this opening. A 2.0 mm hollow female Leur-Loc placed over the dura is fitted to the craniectomy site and anchored to the skull using dental cement.

The Dragonfly Fluid Percussion Device (model # HPD-1700) is attached via a male Leur-Loc to the female Leur-Loc, implanted over the exposed dura of the rat. The device produces a saline pulse of increased intracranial pressure (ICP) of varying volumes into the cranial cavity. Brief displacement and deformation of neural tissue results from the rapid epidural injection of saline. Femoral artery cannulation is performed and blood pressure is recorded throughout the procedure.

There are three levels of severity that can be produced:
Low-grade: 0-1.0 atm
Moderate: 1.5-2.0 atm
High-grade: 2.4-3.0 atm Animals injured at pressures greater than 3.0-3.6 atm will suffer immediate apnea and fail to recover unless assisted by a ventilator Perri et al (Petrausch, B. et al. *J. Neurosci.* 20: 8031-8041, 2000; *J. Neurosci.* 17: 5560-5572, 2000). The applied cortical pressure pulse is measured extracranially by a electronic transducer coupled to an oscilloscope housed in the injury device.

Following FP brain injury, the Luer Loc is removed, the incision is sutured with 4-0 silk, a layer of triple antibiotic ointment is applied to the closure, and the animals are returned to their cages.

Morphometric analysis is performed to quantify infarction. Twenty-four hours after the induction of focal ischemia, rats are deeply anesthetized with $CO_2$ and decapitated. The brain is removed and placed in ice chilled (~4° C.) saline for fifteen minutes. Seven 2.0 mm coronal slices are cut using a brain cutting matrix and incubated in two percent 2,3,5 triphenyltetrazolium chloride (TTC) for 20 minutes at 37° C. Slices are removed, washed in saline and put into 10% formalin for 24 hours before tissue analysis.

TTC is an established marker for functional mitochondrial enzymes and produces a visible deep red color within normal tissue. Injured tissue, lacking mitochondrial activity, remains unstained and appears white. This is a standard method for use in image analysis of the sliced brain and quantification of the ischemic area after MCAo. Using the Image Pro-Plus imaging system, a total of 14 images per brain of both the frontal and posterior side of each slice are analyzed through digital analysis. Digitizing and computation is done under blinded conditions. The total injury volumes are calculated for each animal and subsequent group means are determined as volume of area ($mm^3$). The total injury volume is calculated for the left hemisphere using the equation below.

$$\text{Volume (mm}^3) = \frac{\Sigma \text{area (mm}^2\text{) per side}}{\text{No. of sides analyzed}} \times 14 \text{ mm}$$

Example 8

In Vitro Study of Controllably Buoyant Polymeric Particles

Polymeric carriers containing buoyancy agents are manufactured as discussed in Example 1. To move particles towards and concentrate at the brain and upper regions of the central nervous system, the polymeric particles are manufactured to have a specific gravity less than 1.0063. Particles are made positively buoyant by adding one or more of the following excipients to the polymer matrix: Mineral Oil, Isopropyl Myrisate, Librafil™ 1944, Vegetable Oil, Glycerl Monostearate, Parrafin, Oelic Acid, Methyl Oelate, Lanolin, Petrolatin, Cetyl Alcohol, Corn Oil, Soybean Oil, and Castor Oil, Air, Nitrogen, Argon, Hydrofluorocarbons, Carbon Dioxide, Helium, and Xenon.

To have particles remain neutrally buoyant and have the ability to be carried throughout the CNS by the natural flow of the CSF, particles are manufactured that have a specific gravity between 1.0063 and 1.0075. Particles are made neutrally buoyant by adding one or more of the following excipients to the polymer matrix; a Polysorbate, a Sorbitan Ester, and a Polyoxyethylene Alkyl Ethyl.

To move particles towards and concentrate at the spinal cord and lower regions of the central nervous system, particles are manufactured to have a specific gravity greater than 1.0075. Particles are made negatively buoyant by adding one or more of the following excipients to the polymer matrix; Glycerin, Aliphatic Polyesters, Gelatin, and Mannitol.

Positively buoyant, neutrally buoyant and negatively buoyant polymeric carriers (in this example, microspheres) are separately suspended in a device designed to simulate a patient assuming an upright position. A device with the ability to control flow rates is used to house cerebrospinal fluid. The device has a temperature control that maintains the fluid at 37° C. A pulse may be added to simulate the choroidal pulse from vascular flow. A manometer is included to measure pressures on the proximal side of the valve, to maintain them at normal range. Microspheres are added to the device. Positively buoyant microspheres are seen floating at the top of the device, while neutrally buoyant microspheres are floating at approximately the same location as originally placed. Negatively buoyant microspheres fall towards the bottom of the device. These studies indicate that microspheres are manufactured to move within the CNS and target specific areas of disease state.

Buoyancy is also evaluated as follows. Positively buoyant, neutrally buoyant and negatively buoyant polymeric carriers (in this example, microspheres) are individually suspended in a graduated cylinder containing either sterile saline water or cerebral spinal fluid and brought to 37° C. using a temperature controlled water bath. The microspheres are allowed to flow freely within the graduated cylinder. Positively buoyant microspheres float at the top of the graduated cylinder, while neutrally buoyant microspheres float at approximately the same location as originally located. Negatively buoyant microspheres fall towards the bottom of the graduated cylinder.

Example 9

In Vivo Studies with Fluorescein to Determine Composition Location

Polymer compositions are prepared as described in Example 1. A detectable label, such as a fluorescent moiety, is added during the manufacturing process so that real-time detection of the microspheres is possible. Microspheres that were found to be negatively buoyant, neutrally buoyant and positively buoyant are injected intrathecally to a subject that is maintained in an upright position. After a certain period of time, a diagnostic medical instrument is used to determine the location of the microspheres. In this way, it is possible to determine the anatomical location of the polymer compositions.

What is claimed is:

1. A method for administering a therapeutic agent within the central nervous system of a subject, the method comprising intrathecally administering a composition to the central nervous system of said subject, wherein said composition comprises a plurality of biodegradable polymer particles having a therapeutic agent and a buoyancy agent contained therein, wherein the buoyancy agent is a gas or an oil, or a combination thereof, and wherein the composition is controllably buoyant within the cerebrospinal fluid to provide targeted delivery of the therapeutic agent within the central nervous system of the subject, wherein the buoyancy agent comprises a hydrofluorocarbon.

2. The method of claim 1, wherein said subject is diagnosed with a central nervous system disorder.

3. The method of claim 2, wherein the central nervous system disorder is selected from the group consisting of cancer, Parkinson's disease, Alzheimer's dementia, Huntington's disease, epilepsy, amyotrophic lateral sclerosis, multiple sclerosis, trauma, stroke, traumatic brain injury, depression, spinal cord injury, and pain management.

4. The method of claim 1, wherein the intrathecal administration occurs directly into the cerebrospinal fluid of the subject.

5. The method of claim 1, wherein said biodegradable polymer is a naturally derived polymer selected from the group consisting of albumin, alginate, cellulose, collagen, fibrin, gelatin, and polysaccharides.

6. The method of claim 1, wherein said biodegradable polymer is a synthetic polymer selected from the group consisting of polyesters, polyethylene glycol, poloxomers, polyanhydrides, and pluronics.

7. The method of claim 1, wherein said synthetic polymer is poly(lactide-co-glycolide).

8. The method of claim 1, wherein the therapeutic agent is a neuroprotective agent and said composition is administered to a subject having a central nervous system disorder.

9. The method of claim 1, wherein said composition is in the form of a plurality of spherical particles from about 1 to about 25 μm in diameter.

10. The method of claim 1, wherein the therapeutic agent is selected from the group consisting of L-dopa, dopamine, carbidopa, choline, acetyl choline, cholinergic neuronotropic agents, gangliosides, nerve growth enhancing agents, living cells, enzymes, antipsychotropic agents, antidepressants, excitatory amino acid antagonist or agonist, antiepileptic medications, and combinations thereof as well as antioxidants, nonsteroidal anti-inflammatory drugs (NSAIDS), steroidal anti-inflammatory agents, calcium channel blockers, N-methyl-D-aspartate (NMDA) antagonists, inosine, citicoline, superoxide dismutase, dextrorphan, aspirin, tetramethylpyrazine, antibiotics, and combinations thereof.

11. The method of claim 10, wherein said living cells are selected from bone marrow cells and fetal neural tissue and stem cells, and combinations thereof.

12. The method of claim 1, wherein the therapeutic agent is a cancer agent selected from the group consisting of vinca alkaloids and other plant products, cytostatic drugs, cytotoxic drugs, hormones, alkylating agents, immunomodulators, hematological agents, radiopharmaceuticals, antibodies, antiandrogens, and epidermals.

13. The method of claim 12, wherein said hormones are selected from estrogens and anti-estrogens.

14. The method of claim 12, wherein said immunomodulators are selected from immunostimulators and immunosuppressives.

* * * * *